United States Patent
Andrews et al.

(10) Patent No.: US 11,925,538 B2
(45) Date of Patent: Mar. 12, 2024

(54) APPARATUS AND METHOD OF MANUFACTURING AN ELASTIC COMPOSITE STRUCTURE FOR AN ABSORBENT SANITARY PRODUCT

(71) Applicant: Curt G. Joa, Inc., Sheboygan Falls, WI (US)

(72) Inventors: Robert Earl Andrews, Sheboygan, WI (US); David Edward Schuette, Kiel, WI (US); Jeffrey Wayne Fritz, Plymouth, WI (US); Justin Marshall Lafferty, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 721 days.

(21) Appl. No.: 16/721,414

(22) Filed: Dec. 19, 2019

(65) Prior Publication Data

US 2020/0214901 A1    Jul. 9, 2020

Related U.S. Application Data

(60) Provisional application No. 62/789,058, filed on Jan. 7, 2019.

(51) Int. Cl.
    *A61F 13/15*    (2006.01)
    *B29C 65/08*    (2006.01)
    (Continued)

(52) U.S. Cl.
    CPC .. *A61F 13/15699* (2013.01); *A61F 13/15658* (2013.01); *B29C 65/08* (2013.01);
    (Continued)

(58) Field of Classification Search
    None
    See application file for complete search history.

(56) References Cited

U.S. PATENT DOCUMENTS

| 3,580,783 A | 5/1971 | Glaze |
| 3,589,100 A | 6/1971 | Konars et al. |

(Continued)

FOREIGN PATENT DOCUMENTS

| CN | 101868210 B | 9/2014 |
| EP | 0274752 A2 | 7/1988 |

(Continued)

OTHER PUBLICATIONS

Presentation by Thomas Ehlert, VP of RD&E, Aurizon Ultrasonics, LLC, entitled "Adhesive-free, Ultrasonic Elastic Attachment", date at least as early as Nov. 17, 2014, 57 pages.

(Continued)

*Primary Examiner* — Barbara J Musser
(74) *Attorney, Agent, or Firm* — Klintworth & Rozenblat IP LLP

(57) ABSTRACT

An apparatus and method for manufacturing an elastic composite structure for an absorbent sanitary product includes a bonding unit configured to bond a first web layer to a second web layer via a bond pattern that includes at least one bond line having at least one pair of adjacent bonds. The bonding unit secures an elastic thread within a passage defined by the at least one pair of adjacent bonds. The passage has a cross-sectional area smaller than a cross-sectional area of the elastic thread in a non-tensioned state.

6 Claims, 10 Drawing Sheets

(51) Int. Cl.
 B29C 65/78 (2006.01)
 B29L 31/48 (2006.01)
 B32B 37/00 (2006.01)
 B32B 37/20 (2006.01)

(52) U.S. Cl.
 CPC ...... B29C 65/7894 (2013.01); B32B 37/0076 (2013.01); B32B 37/20 (2013.01); *A61F 2013/15869* (2013.01); *A61F 2013/15991* (2013.01); *B29L 2031/4878* (2013.01); *B32B 2307/51* (2013.01); *B32B 2555/02* (2013.01)

(56) References Cited

U.S. PATENT DOCUMENTS

| | | |
|---|---|---|
| 3,622,434 A | 11/1971 | Newman |
| 3,658,064 A | 4/1972 | Pociluyko |
| 3,668,054 A | 6/1972 | Stumpf |
| 3,844,869 A | 10/1974 | Rust, Jr. |
| 3,884,227 A | 5/1975 | Lutz et al. |
| 3,982,988 A | 9/1976 | Heimberger |
| 3,993,532 A | 11/1976 | McDonald et al. |
| 4,088,731 A | 5/1978 | Groome |
| 4,305,988 A | 12/1981 | Kocher |
| 4,305,998 A | 12/1981 | Manty et al. |
| 4,333,978 A | 6/1982 | Kocher |
| 4,336,203 A | 6/1982 | Zucker et al. |
| 4,443,291 A | 4/1984 | Reed |
| 4,485,819 A | 12/1984 | Igl |
| 4,662,005 A | 5/1987 | Grier-Idris |
| 4,770,656 A | 9/1988 | Proxmire et al. |
| 4,808,176 A | 2/1989 | Kielpikowski |
| 4,833,734 A | 5/1989 | Der Estephanian |
| 4,834,738 A | 5/1989 | Kielpikowski et al. |
| 4,834,741 A | 5/1989 | Sabee |
| 4,842,596 A | 6/1989 | Kielpikowski et al. |
| 4,863,542 A | 9/1989 | Oshefsky et al. |
| 4,919,738 A | 4/1990 | Ball et al. |
| 4,977,011 A | 12/1990 | Smith |
| 5,094,717 A | 3/1992 | Manning et al. |
| 5,163,932 A | 11/1992 | Nomura et al. |
| 5,353,798 A | 10/1994 | Sieben |
| 5,468,320 A | 11/1995 | Zafiroglu |
| 5,530,979 A | 7/1996 | Whitley |
| 5,561,863 A | 10/1996 | Carlson, II |
| 5,618,378 A | 4/1997 | Cahill |
| 5,624,420 A | 4/1997 | Bridges et al. |
| 5,643,395 A | 7/1997 | Hinton |
| 5,643,396 A | 7/1997 | Rajala et al. |
| 5,660,657 A | 8/1997 | Rajala et al. |
| 5,694,925 A | 12/1997 | Reese et al. |
| 5,699,791 A | 12/1997 | Sukiennik et al. |
| 5,707,470 A | 1/1998 | Rajala et al. |
| 5,711,847 A | 1/1998 | Rajala et al. |
| 5,745,922 A | 5/1998 | Rajala et al. |
| 5,769,993 A | 6/1998 | Baldauf |
| 5,789,065 A | 8/1998 | Haffner et al. |
| 5,797,895 A | 8/1998 | Widlund et al. |
| 5,803,075 A | 9/1998 | Yavitz |
| 5,813,398 A | 9/1998 | Baird et al. |
| 5,817,584 A | 10/1998 | Singer et al. |
| 5,883,026 A | 3/1999 | Reader et al. |
| 5,934,275 A | 8/1999 | Gazzara |
| 5,954,055 A | 9/1999 | Miyake |
| D424,688 S | 5/2000 | Bryant et al. |
| 6,055,982 A | 5/2000 | Brunson et al. |
| 6,057,024 A | 5/2000 | Mleziva et al. |
| 6,062,220 A | 5/2000 | Whitaker et al. |
| 6,123,077 A | 9/2000 | Bostock et al. |
| 6,125,849 A | 10/2000 | Williams et al. |
| 6,165,298 A | 12/2000 | Samida et al. |
| 6,173,712 B1 | 1/2001 | Brunson |
| 6,197,404 B1 | 3/2001 | Varona |
| 6,213,125 B1 | 4/2001 | Reese et al. |
| 6,217,889 B1 | 4/2001 | Lorenzi et al. |
| 6,235,137 B1 | 5/2001 | Van Eperen et al. |
| 6,257,235 B1 | 7/2001 | Bowen |
| 6,279,570 B1 | 8/2001 | Mittelstadt et al. |
| 6,291,039 B1 | 9/2001 | Combe et al. |
| 6,295,714 B1 | 10/2001 | Roychowdhury et al. |
| 6,332,465 B1 | 12/2001 | Xue et al. |
| 6,340,782 B1 | 1/2002 | Kling et al. |
| 6,354,296 B1 | 3/2002 | Baumann et al. |
| 6,394,090 B1 | 5/2002 | Chen et al. |
| 6,427,693 B1 | 8/2002 | Blackstock et al. |
| 6,460,539 B1 | 10/2002 | Japuntich et al. |
| 6,482,278 B1 | 11/2002 | McCabe et al. |
| 6,484,722 B2 | 11/2002 | Bostock et al. |
| 6,506,474 B2 | 1/2003 | Tsuji |
| 6,534,694 B2 | 3/2003 | Kling et al. |
| 6,536,434 B1 | 3/2003 | Bostock et al. |
| 6,541,679 B2 | 4/2003 | Betrabet et al. |
| 6,568,392 B1 | 5/2003 | Bostock et al. |
| 6,584,976 B2 | 7/2003 | Japuntich et al. |
| 6,604,524 B1 | 8/2003 | Curran et al. |
| 6,613,955 B1 | 9/2003 | Lindsay et al. |
| 6,623,837 B2 | 9/2003 | Morman et al. |
| 6,644,314 B1 | 11/2003 | Elsberg |
| 6,652,693 B2 | 11/2003 | Burriss et al. |
| 6,673,980 B1 | 1/2004 | Varona et al. |
| 6,676,062 B1 | 1/2004 | Herhaus |
| 6,701,992 B1 | 3/2004 | Pasquale et al. |
| 6,712,922 B2 | 3/2004 | Sorenson et al. |
| 6,715,489 B2 | 4/2004 | Bostock et al. |
| 6,722,366 B2 | 4/2004 | Bostock et al. |
| 6,730,188 B2 | 5/2004 | Sanders |
| 6,761,710 B2 | 7/2004 | Acchioli et al. |
| 6,780,263 B2 | 8/2004 | Delisle |
| 6,843,872 B2 | 1/2005 | Morman |
| 6,886,563 B2 | 5/2005 | Bostock et al. |
| 6,889,622 B2 | 5/2005 | Marcangelo |
| 6,914,018 B1 | 7/2005 | Uitenbroek et al. |
| 6,928,657 B2 | 8/2005 | Bell et al. |
| 6,953,452 B2 | 10/2005 | Popp et al. |
| 7,008,496 B2 | 3/2006 | Morman |
| 7,021,227 B2 | 4/2006 | Marcangelo |
| 7,025,841 B2 | 4/2006 | Owen |
| 7,044,131 B2 | 5/2006 | Griesbach et al. |
| 7,069,930 B2 | 7/2006 | Bostock et al. |
| 7,118,558 B2 | 10/2006 | Wu et al. |
| 7,198,688 B2 | 4/2007 | Mortell et al. |
| 7,211,531 B2 | 5/2007 | Schneider et al. |
| 7,217,261 B2 | 5/2007 | Otsubo et al. |
| 7,290,545 B2 | 11/2007 | Kleman et al. |
| 7,316,840 B2 | 1/2008 | Neculescu et al. |
| 7,361,241 B2 | 4/2008 | Barth et al. |
| 7,378,566 B2 | 5/2008 | Soerens et al. |
| 7,464,516 B2 | 12/2008 | Johnson |
| 7,469,427 B2 | 12/2008 | Yang et al. |
| 7,507,680 B2 | 3/2009 | Middlesworth et al. |
| 7,582,348 B2 | 9/2009 | Ando et al. |
| 7,617,787 B2 | 11/2009 | Marcangelo |
| 7,619,167 B2 | 11/2009 | Lee et al. |
| 7,638,014 B2 | 12/2009 | Coose et al. |
| 7,642,398 B2 | 1/2010 | Jarpenberg et al. |
| 7,691,138 B2 | 4/2010 | Stenzel et al. |
| 7,708,849 B2 | 5/2010 | McCabe |
| 7,722,734 B2 | 5/2010 | Otsubo |
| 7,725,948 B2 | 6/2010 | Steindorf |
| 7,799,967 B2 | 9/2010 | Ranganathan et al. |
| 7,833,369 B2 | 11/2010 | Zhou et al. |
| 7,845,351 B2 | 12/2010 | Mathis et al. |
| 7,861,756 B2 | 1/2011 | Jenquin et al. |
| 7,901,392 B2 | 3/2011 | Kline et al. |
| 7,955,418 B2 | 6/2011 | Claussen et al. |
| 7,981,231 B2 | 7/2011 | Schneider et al. |
| 8,007,484 B2 | 8/2011 | McCabe et al. |
| 8,074,660 B2 | 12/2011 | Duffy |
| 8,075,543 B2 | 12/2011 | Okuda |
| 8,091,550 B2 | 1/2012 | Steindorf |
| 8,109,916 B2 | 2/2012 | Wennerbaeck |
| 8,142,411 B2 | 3/2012 | Kline et al. |
| 8,146,594 B2 | 4/2012 | Bostock et al. |
| 8,182,457 B2 | 5/2012 | Olson et al. |
| 8,182,624 B2 | 5/2012 | Handziak |

(56) References Cited

U.S. PATENT DOCUMENTS

| | | |
|---|---|---|
| 8,207,395 B2 | 6/2012 | Soerens et al. |
| 8,268,444 B2 | 9/2012 | Okaya |
| 8,282,617 B2 | 10/2012 | Kaneda |
| 8,298,205 B2 | 10/2012 | Norrby et al. |
| 8,308,706 B2 | 11/2012 | Fukae |
| 8,323,257 B2 | 12/2012 | Melik et al. |
| 8,328,820 B2 | 12/2012 | Diamant et al. |
| 8,360,067 B2 | 1/2013 | Duffy |
| 8,375,950 B2 | 2/2013 | Bostock et al. |
| 8,435,223 B2 | 5/2013 | Roe et al. |
| 8,440,043 B1 | 5/2013 | Schneider et al. |
| 8,470,946 B1 | 6/2013 | Carlson |
| 8,528,560 B2 | 9/2013 | Duffy |
| 8,562,777 B2 | 10/2013 | Drake |
| 8,585,667 B2 | 11/2013 | Roe et al. |
| 8,622,059 B2 | 1/2014 | Kleman |
| 8,640,704 B2 | 2/2014 | Spoo et al. |
| 8,647,319 B2 | 2/2014 | Een et al. |
| 8,652,114 B2 | 2/2014 | Roe et al. |
| 8,652,115 B2 | 2/2014 | Roe et al. |
| 8,669,409 B2 | 3/2014 | Roe |
| 8,702,671 B2 | 4/2014 | Tsang et al. |
| 8,740,128 B2 | 6/2014 | Oravits et al. |
| 8,741,083 B2 | 6/2014 | Wennerbaeck et al. |
| 8,758,786 B2 | 6/2014 | Hassler |
| 8,771,449 B2 | 7/2014 | Takino et al. |
| 8,784,395 B2 | 7/2014 | Roe et al. |
| 8,784,397 B2 | 7/2014 | Chang et al. |
| 8,808,263 B2 | 8/2014 | Roe et al. |
| 8,881,729 B2 | 11/2014 | Duffy |
| 8,926,579 B2 | 1/2015 | Wang et al. |
| 8,932,273 B2 | 1/2015 | Roe et al. |
| 8,936,586 B2 | 1/2015 | Roe |
| 8,992,497 B2 | 3/2015 | Roe et al. |
| 8,998,870 B2 | 4/2015 | Roe |
| 9,011,402 B2 | 4/2015 | Roe et al. |
| 9,011,404 B2 | 4/2015 | Kobayashi et al. |
| 9,012,013 B2 | 4/2015 | Duffy |
| 9,028,462 B2 | 5/2015 | Poole et al. |
| 9,056,033 B2 | 6/2015 | Fenske |
| 9,060,905 B2 | 6/2015 | Wang et al. |
| 9,078,789 B2 | 7/2015 | Wang et al. |
| 9,078,792 B2 | 7/2015 | Ruiz |
| 9,089,456 B2 | 7/2015 | Roe et al. |
| 9,095,478 B2 | 8/2015 | Roe |
| 9,180,059 B2 | 11/2015 | Roe et al. |
| 9,301,881 B2 | 4/2016 | Ando et al. |
| 9,387,138 B2 | 7/2016 | Roe |
| 9,539,735 B2 | 1/2017 | Ferguson et al. |
| 9,603,395 B2 | 3/2017 | Duffy |
| 9,603,396 B2 | 3/2017 | Duffy |
| 9,615,612 B2 | 4/2017 | Duffy |
| 9,770,057 B2 | 9/2017 | Duffy |
| 9,770,058 B2 | 9/2017 | Angadjivand et al. |
| 9,770,611 B2 | 9/2017 | Facer et al. |
| 9,809,414 B2 | 11/2017 | Fritz et al. |
| 9,868,002 B2 | 1/2018 | Duffy |
| 9,913,764 B2 | 3/2018 | Thomas et al. |
| 10,040,621 B2 | 8/2018 | Duffy et al. |
| 10,130,833 B2 | 11/2018 | Angadjivand et al. |
| 10,137,321 B2 | 11/2018 | Martin |
| 10,143,246 B2 | 12/2018 | Houde et al. |
| D837,970 S | 1/2019 | Henderson et al. |
| 10,182,603 B2 | 1/2019 | Duffy |
| 10,213,348 B2 | 2/2019 | Gualtieri et al. |
| 10,227,202 B2 | 3/2019 | Pamperin et al. |
| 10,259,165 B2 | 4/2019 | Ehlert et al. |
| D848,678 S | 5/2019 | Andrews |
| 10,314,346 B2 | 6/2019 | Potnis et al. |
| 10,329,110 B2 | 6/2019 | Dotta |
| 10,457,436 B2 | 10/2019 | Spencer et al. |
| 10,492,547 B2 | 12/2019 | Weber et al. |
| 10,494,221 B2 | 12/2019 | Harris et al. |
| 10,518,996 B2 | 12/2019 | Adami |
| 10,537,479 B2 | 1/2020 | Schuette et al. |
| 10,596,045 B2 | 3/2020 | Koshijima et al. |
| 10,596,047 B2 | 3/2020 | Coenen et al. |
| 10,751,228 B2 | 8/2020 | Kurohara et al. |
| 10,758,428 B2 | 9/2020 | Nakamura et al. |
| 10,786,398 B2 | 9/2020 | Koshijima et al. |
| 10,792,194 B2 | 10/2020 | Hohm et al. |
| 10,889,066 B2 | 1/2021 | Begrow et al. |
| 10,893,986 B2 | 1/2021 | Manabe et al. |
| 10,973,703 B2 | 4/2021 | Coenen et al. |
| 11,020,281 B2 | 6/2021 | Ishikawa |
| 11,020,286 B2 | 6/2021 | Kaufman et al. |
| 11,117,771 B2 | 9/2021 | Hada et al. |
| 11,129,753 B2 | 9/2021 | Schneider et al. |
| 11,141,321 B2 | 10/2021 | Schneider et al. |
| 11,147,717 B2 | 10/2021 | Schneider et al. |
| 11,173,072 B2 | 11/2021 | Fritz |
| 11,191,676 B2 | 12/2021 | Koshijima et al. |
| 11,219,555 B2 | 1/2022 | Schneider et al. |
| 11,254,062 B2 | 2/2022 | Ehlert et al. |
| 11,254,066 B2 | 2/2022 | Begrow et al. |
| 11,399,989 B2 | 8/2022 | Polidori et al. |
| 11,433,620 B2 | 9/2022 | Ehlert et al. |
| 11,701,268 B2 | 7/2023 | Andrews et al. |
| 2001/0025683 A1 | 10/2001 | Burriss et al. |
| 2001/0034508 A1 | 10/2001 | Betrabet et al. |
| 2001/0044250 A1 | 11/2001 | Tsuji |
| 2002/0092604 A1 | 7/2002 | McCabe et al. |
| 2002/0116027 A1 | 8/2002 | Egan et al. |
| 2002/0117575 A1 | 8/2002 | Gilmore et al. |
| 2002/0119288 A1 | 8/2002 | Morman et al. |
| 2002/0157778 A1 | 10/2002 | Sorenson et al. |
| 2003/0051803 A1 | 3/2003 | Sanders |
| 2003/0120250 A1 | 6/2003 | Betrabet et al. |
| 2003/0124306 A1 | 7/2003 | Morman |
| 2003/0125706 A1 | 7/2003 | Popp et al. |
| 2003/0125707 A1 | 7/2003 | Popp et al. |
| 2003/0135185 A1 | 7/2003 | Crowther |
| 2003/0144643 A1 | 7/2003 | Jarpenberg et al. |
| 2004/0005832 A1 | 1/2004 | Neculescu et al. |
| 2004/0059280 A1 | 3/2004 | Makower et al. |
| 2004/0112509 A1 | 6/2004 | Morman |
| 2004/0116885 A1 | 6/2004 | Soerens et al. |
| 2004/0127614 A1 | 7/2004 | Jiang et al. |
| 2004/0138635 A1 | 7/2004 | Soerens et al. |
| 2004/0158217 A1 | 8/2004 | Wu et al. |
| 2004/0192140 A1 | 9/2004 | Schneider et al. |
| 2004/0219854 A1 | 11/2004 | Groitzsch et al. |
| 2004/0226645 A1 | 11/2004 | Owen |
| 2004/0243085 A1 | 12/2004 | Veith et al. |
| 2004/0261230 A1 | 12/2004 | Neeb et al. |
| 2005/0095942 A1 | 5/2005 | Mueller et al. |
| 2005/0101216 A1 | 5/2005 | Middlesworth et al. |
| 2005/0131374 A1 | 6/2005 | Otsubo et al. |
| 2005/0142331 A1 | 6/2005 | Anderson et al. |
| 2005/0148261 A1 | 7/2005 | Close et al. |
| 2005/0176029 A1 | 8/2005 | Heller et al. |
| 2005/0183646 A1 | 8/2005 | Marcangelo |
| 2005/0216058 A1 | 9/2005 | Egan et al. |
| 2005/0228350 A1 | 10/2005 | Ranganathan et al. |
| 2006/0009104 A1 | 1/2006 | Schneider et al. |
| 2006/0069373 A1 | 3/2006 | Schlinz et al. |
| 2006/0099871 A1 | 5/2006 | Porouthoor et al. |
| 2006/0130964 A1 | 6/2006 | McCabe |
| 2006/0135923 A1 | 6/2006 | Boggs et al. |
| 2006/0135932 A1 | 6/2006 | Abuto et al. |
| 2006/0138693 A1 | 6/2006 | Tuman et al. |
| 2006/0149208 A1 | 7/2006 | Carr |
| 2006/0180068 A1 | 8/2006 | Marcangelo |
| 2006/0184149 A1 | 8/2006 | Kasai et al. |
| 2006/0224137 A1 | 10/2006 | McCabe et al. |
| 2006/0228969 A1 | 10/2006 | Erdman |
| 2006/0238757 A1 | 10/2006 | Silcott |
| 2006/0270302 A1 | 11/2006 | Ando et al. |
| 2007/0000021 A1 | 1/2007 | Yang et al. |
| 2007/0068529 A1 | 3/2007 | Kalatoor et al. |
| 2007/0131335 A1 | 6/2007 | Zhou et al. |
| 2007/0175477 A1 | 8/2007 | Baggett |
| 2007/0218245 A1 | 9/2007 | Schneider et al. |
| 2007/0286987 A1 | 12/2007 | Anderson et al. |

(56) References Cited

U.S. PATENT DOCUMENTS

| | | |
|---|---|---|
| 2008/0103460 A1 | 5/2008 | Close et al. |
| 2008/0110554 A1 | 5/2008 | Otsubo |
| 2008/0169373 A1 | 7/2008 | Andrews et al. |
| 2008/0262455 A1 | 10/2008 | Soerens et al. |
| 2008/0312625 A1 | 12/2008 | Hundorf et al. |
| 2009/0134049 A1 | 5/2009 | Melik et al. |
| 2009/0163940 A1 | 6/2009 | Sliwa |
| 2009/0208703 A1 | 8/2009 | Wennerbaeck et al. |
| 2009/0242098 A1 | 10/2009 | Handziak |
| 2009/0306616 A1 | 12/2009 | Wennerbaeck |
| 2009/0326503 A1 | 12/2009 | Lakso et al. |
| 2009/0326504 A1 | 12/2009 | Kaneda |
| 2010/0015190 A1 | 1/2010 | Hassler |
| 2010/0076390 A1 | 3/2010 | Norrby et al. |
| 2010/0076394 A1 | 3/2010 | Hayase et al. |
| 2010/0087352 A1 | 4/2010 | Mason |
| 2010/0286709 A1 | 11/2010 | Diamant et al. |
| 2010/0298798 A1 | 11/2010 | Lakso et al. |
| 2010/0324513 A1 | 12/2010 | Wennerbaeck |
| 2011/0055998 A1 | 3/2011 | Tai et al. |
| 2011/0061786 A1 | 3/2011 | Mason |
| 2011/0067797 A1 | 3/2011 | Schneider et al. |
| 2011/0118689 A1 | 5/2011 | Een et al. |
| 2011/0152811 A1 | 6/2011 | Bing-Wo et al. |
| 2011/0184372 A1 | 7/2011 | Esping et al. |
| 2011/0192888 A1 | 8/2011 | Tai et al. |
| 2011/0251576 A1 | 10/2011 | Ando et al. |
| 2011/0257616 A1 | 10/2011 | Lakso et al. |
| 2012/0088103 A1 | 4/2012 | Sugiura et al. |
| 2012/0095429 A1 | 4/2012 | Kobayashi et al. |
| 2012/0123367 A1 | 5/2012 | Melik et al. |
| 2012/0123368 A1 | 5/2012 | Melik et al. |
| 2012/0123369 A1 | 5/2012 | Melik et al. |
| 2012/0123370 A1 | 5/2012 | Melik et al. |
| 2012/0123371 A1 | 5/2012 | Melik et al. |
| 2012/0123372 A1 | 5/2012 | Melik et al. |
| 2012/0123373 A1 | 5/2012 | Melik et al. |
| 2012/0175064 A1 | 7/2012 | Yamamoto |
| 2012/0228988 A1 | 9/2012 | Cutsforth |
| 2012/0321856 A1 | 12/2012 | Afshari |
| 2012/0328841 A1 | 12/2012 | Afshari |
| 2012/0328842 A1 | 12/2012 | Afshari |
| 2013/0011601 A1 | 1/2013 | Fenske |
| 2013/0012899 A1 | 1/2013 | Fenske |
| 2013/0042411 A1 | 2/2013 | Vitale |
| 2013/0048191 A1 | 2/2013 | Durrance et al. |
| 2013/0079797 A1 | 3/2013 | Diamant et al. |
| 2013/0157012 A1 | 6/2013 | Qin et al. |
| 2013/0165896 A1 | 6/2013 | Carbonari |
| 2013/0255865 A1 | 10/2013 | Brown et al. |
| 2014/0093687 A1 | 4/2014 | Humiston et al. |
| 2014/0099469 A1 | 4/2014 | Abuto et al. |
| 2014/0102650 A1 | 4/2014 | Qin et al. |
| 2014/0180126 A1 | 6/2014 | Millett et al. |
| 2015/0050462 A1 | 2/2015 | Schroer, Jr. |
| 2015/0164705 A1 | 6/2015 | Thomas et al. |
| 2016/0058624 A1 | 3/2016 | Hohm et al. |
| 2016/0228305 A1 | 8/2016 | Gualtieri et al. |
| 2016/0288407 A1 | 10/2016 | Ehlert et al. |
| 2016/0331600 A1 | 11/2016 | Polidori et al. |
| 2017/0113366 A1 | 4/2017 | Ferguson et al. |
| 2017/0281417 A1 | 10/2017 | Ishikawa |
| 2018/0027899 A1 | 2/2018 | Facer et al. |
| 2018/0042788 A1 | 2/2018 | Kurohara et al. |
| 2018/0093444 A1 | 4/2018 | Begrow et al. |
| 2018/0140473 A1 | 5/2018 | Koshijima et al. |
| 2018/0147095 A1 | 5/2018 | Koshijima et al. |
| 2018/0168880 A1 | 6/2018 | Schneider et al. |
| 2018/0169964 A1 | 6/2018 | Schneider et al. |
| 2018/0170027 A1 | 6/2018 | Schneider et al. |
| 2018/0280209 A1 | 10/2018 | Manabe et al. |
| 2019/0000162 A1 | 1/2019 | Houde |
| 2019/0021916 A1 | 1/2019 | Ishikawa |
| 2019/0070041 A1 | 3/2019 | Schneider et al. |
| 2019/0209396 A1 | 7/2019 | Nakamura et al. |
| 2019/0224053 A1 | 7/2019 | Nakamura et al. |
| 2019/0231606 A1 | 8/2019 | Andrews et al. |
| 2019/0274895 A1 | 9/2019 | Chen et al. |
| 2019/0358093 A1 | 11/2019 | Kaufman et al. |
| 2019/0374398 A1 | 12/2019 | Coenen et al. |
| 2019/0374404 A1 | 12/2019 | Ninomiya et al. |
| 2020/0039152 A1 | 2/2020 | Ehlert et al. |
| 2020/0179180 A1* | 6/2020 | Koshijima ............... B32B 5/022 |
| 2020/0197230 A1 | 6/2020 | Ohtsubo |
| 2020/0206040 A1 | 7/2020 | Andrews et al. |
| 2020/0206043 A1 | 7/2020 | Coenen et al. |
| 2020/0268567 A1 | 8/2020 | Coenen et al. |
| 2020/0297551 A1 | 9/2020 | Andrews et al. |
| 2020/0298545 A1 | 9/2020 | Andrews et al. |
| 2020/0299883 A1 | 9/2020 | Begrow et al. |
| 2020/0360191 A1 | 11/2020 | Nakamura et al. |
| 2020/0361158 A1 | 11/2020 | Sugiura et al. |
| 2021/0000657 A1 | 1/2021 | Hohm et al. |
| 2021/0059866 A1 | 3/2021 | Fritz et al. |
| 2021/0100695 A1 | 4/2021 | Ishibashi et al. |
| 2021/0205152 A1 | 7/2021 | Polidori et al. |
| 2021/0252796 A1 | 8/2021 | Ehlert et al. |
| 2021/0267818 A1 | 9/2021 | Kaufman et al. |
| 2022/0000676 A1 | 1/2022 | Schneider et al. |
| 2022/0071809 A1 | 3/2022 | Fritz |
| 2022/0151840 A1 | 5/2022 | Mueller et al. |
| 2022/0211553 A1 | 7/2022 | Manabe |
| 2022/0218534 A1 | 7/2022 | Minami et al. |
| 2022/0250331 A1 | 8/2022 | Weiler et al. |
| 2022/0324669 A1 | 10/2022 | Follen et al. |
| 2023/0339714 A1 | 10/2023 | Roehrborn et al. |

FOREIGN PATENT DOCUMENTS

| | | |
|---|---|---|
| EP | 0330716 A2 | 9/1989 |
| EP | 0168225 B1 | 3/1991 |
| EP | 0307871 B1 | 12/1992 |
| EP | 0386324 B1 | 6/1993 |
| EP | 0685586 A2 | 12/1995 |
| EP | 0677284 B1 | 6/1999 |
| EP | 0886480 B1 | 12/2001 |
| EP | 1166721 A2 | 1/2002 |
| EP | 1035808 B1 | 3/2004 |
| EP | 1024721 B1 | 9/2004 |
| EP | 1351815 B1 | 2/2005 |
| EP | 1555000 A2 | 7/2005 |
| EP | 1388410 B1 | 10/2005 |
| EP | 1448824 B1 | 10/2005 |
| EP | 1236827 B1 | 1/2006 |
| EP | 1029521 B1 | 4/2006 |
| EP | 1138471 B1 | 6/2006 |
| EP | 1159942 B1 | 7/2006 |
| EP | 1641417 B1 | 6/2007 |
| EP | 1547558 B1 | 10/2008 |
| EP | 1290289 B1 | 12/2008 |
| EP | 1330355 B1 | 3/2009 |
| EP | 1263989 B1 | 5/2009 |
| EP | 1330222 B1 | 8/2009 |
| EP | 1458553 B1 | 9/2009 |
| EP | 2103427 A2 | 9/2009 |
| EP | 1610950 B1 | 10/2009 |
| EP | 1715994 B1 | 3/2010 |
| EP | 1520569 B1 | 7/2010 |
| EP | 1586252 B1 | 8/2010 |
| EP | 1959907 B1 | 9/2010 |
| EP | 1525345 B1 | 4/2011 |
| EP | 1882177 B1 | 6/2011 |
| EP | 1707168 B1 | 8/2011 |
| EP | 1716831 B1 | 9/2011 |
| EP | 2083100 B1 | 9/2011 |
| EP | 2207926 B1 | 9/2011 |
| EP | 2219534 B1 | 9/2011 |
| EP | 2027841 B1 | 7/2012 |
| EP | 1595017 B1 | 8/2012 |
| EP | 1891256 B1 | 8/2012 |
| EP | 2020972 B1 | 11/2012 |
| EP | 2020974 B1 | 12/2012 |
| EP | 1685816 B1 | 1/2013 |
| EP | 2024178 B1 | 1/2013 |

(56) References Cited

FOREIGN PATENT DOCUMENTS

| | | |
|---|---|---|
| EP | 2088980 B1 | 1/2013 |
| EP | 1272347 B1 | 4/2013 |
| EP | 1458565 B1 | 3/2014 |
| EP | 2727521 A1 | 5/2014 |
| EP | 1575470 B1 | 6/2014 |
| EP | 2088981 B1 | 6/2014 |
| EP | 2431013 B1 | 9/2014 |
| EP | 2441866 B1 | 2/2015 |
| EP | 2133297 B1 | 4/2016 |
| EP | 1806117 B1 | 6/2016 |
| EP | 3028687 A1 | 6/2016 |
| EP | 3092997 A1 | 11/2016 |
| EP | 1666178 B1 | 5/2017 |
| EP | 2214614 B1 | 8/2017 |
| EP | 2450015 B1 | 11/2017 |
| EP | 2105115 B1 | 3/2018 |
| EP | 3299167 A1 | 3/2018 |
| EP | 2116367 B1 | 4/2018 |
| EP | 2142261 B1 | 5/2018 |
| EP | 2454957 B1 | 11/2018 |
| EP | 3117810 B1 | 7/2019 |
| EP | 3527181 A1 | 8/2019 |
| EP | 3199132 B1 | 9/2019 |
| EP | 3056176 B1 | 10/2019 |
| EP | 3296100 B1 | 1/2020 |
| EP | 3646830 A1 | 5/2020 |
| EP | 3677231 A1 | 7/2020 |
| EP | 3747636 A1 | 12/2020 |
| EP | 3558192 B1 | 1/2021 |
| EP | 3558664 B1 | 4/2021 |
| EP | 3519162 B1 | 7/2021 |
| EP | 3572052 B1 | 7/2021 |
| EP | 3558193 B1 | 8/2021 |
| EP | 3865103 A1 | 8/2021 |
| EP | 3558191 B1 | 9/2021 |
| EP | 3275413 B1 | 10/2021 |
| EP | 3342385 B1 | 10/2021 |
| EP | 3527182 B1 | 10/2021 |
| EP | 3675785 B1 | 11/2021 |
| EP | 3904057 A1 | 11/2021 |
| EP | 3960140 A1 | 3/2022 |
| EP | 3960439 A1 | 3/2022 |
| EP | 3981371 A1 | 4/2022 |
| EP | 3675784 B1 | 10/2022 |
| FR | 2532337 A1 | 3/1984 |
| JP | 2005095574 A | 4/2005 |
| JP | 2008154998 A | 7/2008 |
| JP | 2009056156 A | 3/2009 |
| JP | 2009106667 A | 5/2009 |
| JP | 5085239 B2 | 11/2012 |
| JP | 05106990 B2 | 12/2012 |
| JP | 05124188 B2 | 1/2013 |
| JP | 2014198179 A | 10/2014 |
| JP | 2017064130 A | 4/2017 |
| JP | 06192003 B2 | 9/2017 |
| JP | 2019030441 A | 2/2019 |
| KR | 1982464 B1 | 5/2019 |
| KR | 2013608 B1 | 8/2019 |
| KR | 2022211 B1 | 9/2019 |
| RU | 2304047 C2 | 8/2007 |
| RU | 2010125133 A | 12/2011 |
| WO | WO1993021788 A1 | 11/1993 |
| WO | WO0192013 A1 | 12/2001 |
| WO | WO2009067055 A1 | 5/2009 |
| WO | WO2011087502 A1 | 7/2011 |
| WO | 2014109924 A1 | 7/2014 |
| WO | WO2014145668 A1 | 9/2014 |
| WO | 2016033226 A1 | 3/2016 |
| WO | 2016109514 A1 | 7/2016 |
| WO | WO2016160752 A1 | 10/2016 |
| WO | 2016208513 A1 | 12/2016 |
| WO | WO2018097771 A1 | 5/2018 |
| WO | 2018118431 A1 | 6/2018 |
| WO | WO2018118573 A1 | 6/2018 |
| WO | 2018/154680 A1 | 8/2018 |
| WO | WO2018160207 A1 | 9/2018 |
| WO | WO2018160208 A1 | 9/2018 |
| WO | WO2019070248 A1 | 4/2019 |
| WO | WO2019125415 A1 | 6/2019 |
| WO | WO2020198025 A1 | 10/2020 |
| WO | WO2021043943 A1 | 3/2021 |

OTHER PUBLICATIONS

Japanese Office Action for Application No. JP2020-541440 dated Feb. 7, 2023.
PCT International Search Report and Written Opinion, PCT/US2015/047015, dated Nov. 24, 2015, 8 pages.
Notification of Reasons for Refusal issued in Japanese Application No. 2020-147443, dated Oct. 23, 2023, 5 pages.

* cited by examiner

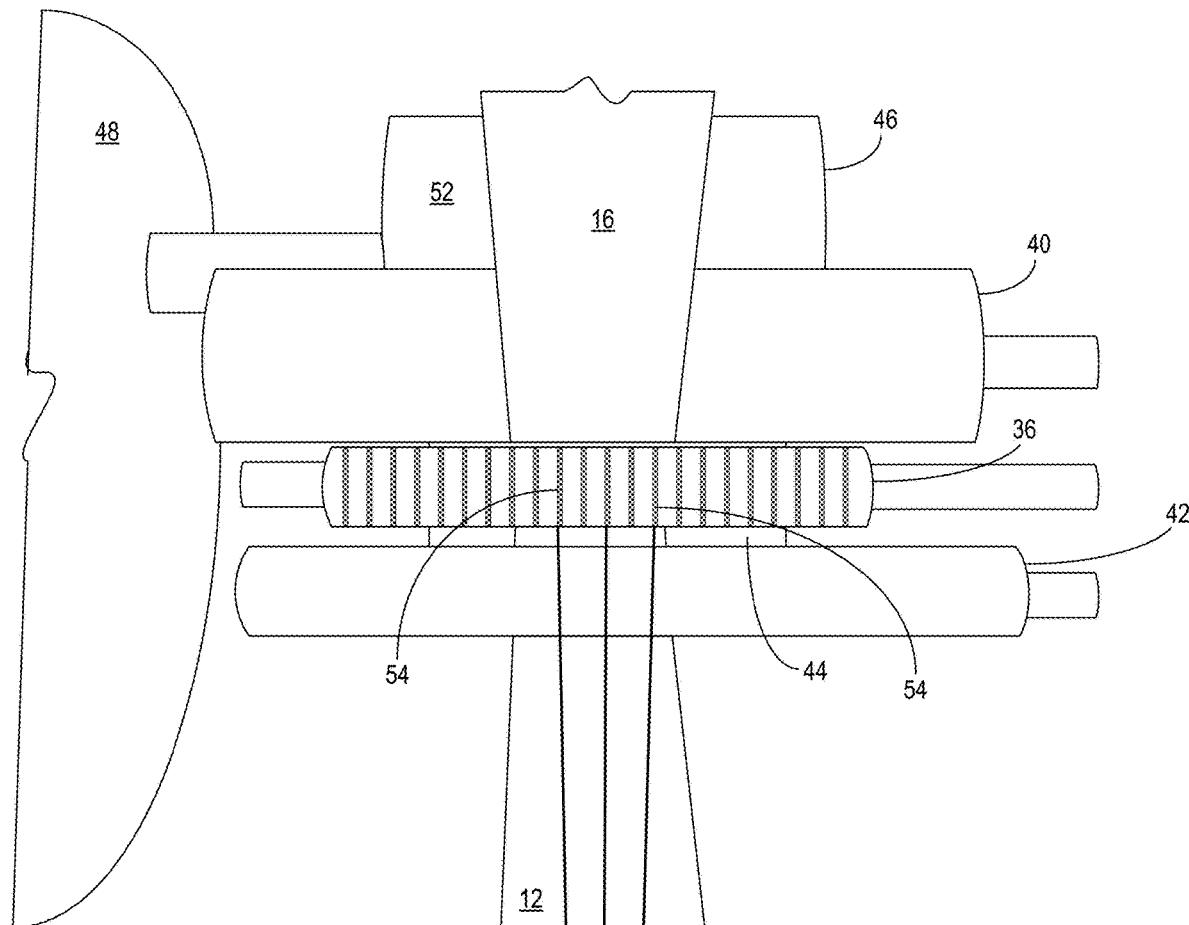
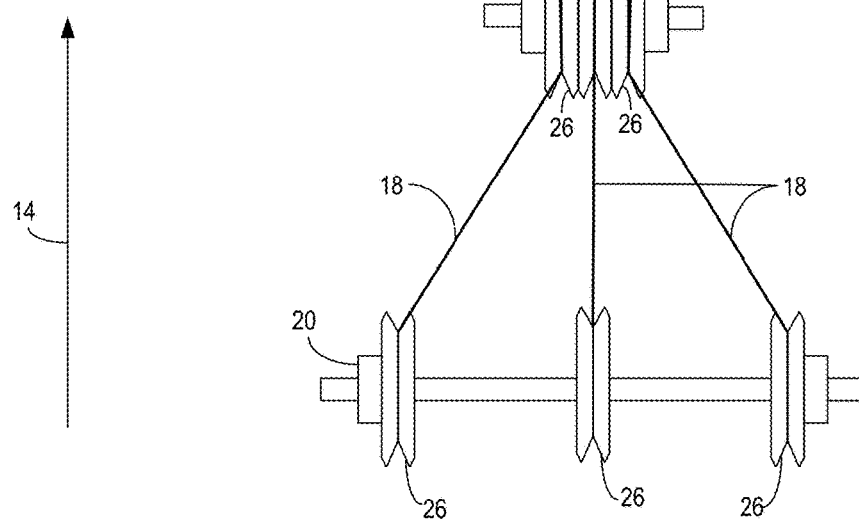
FIG. 2

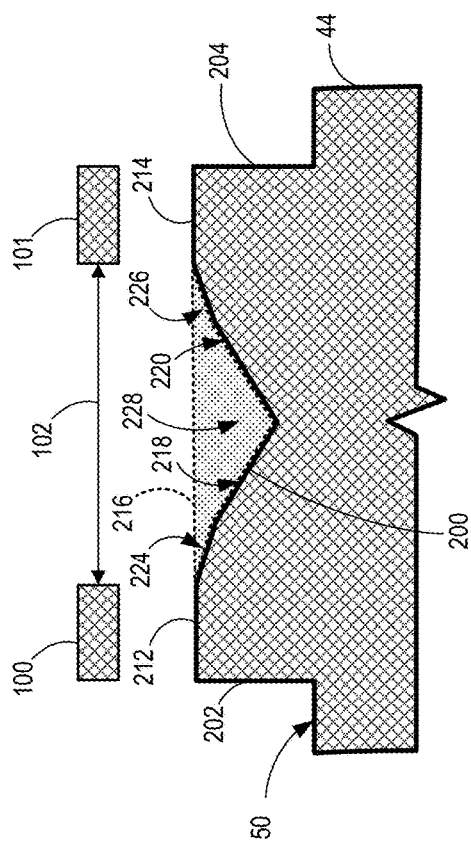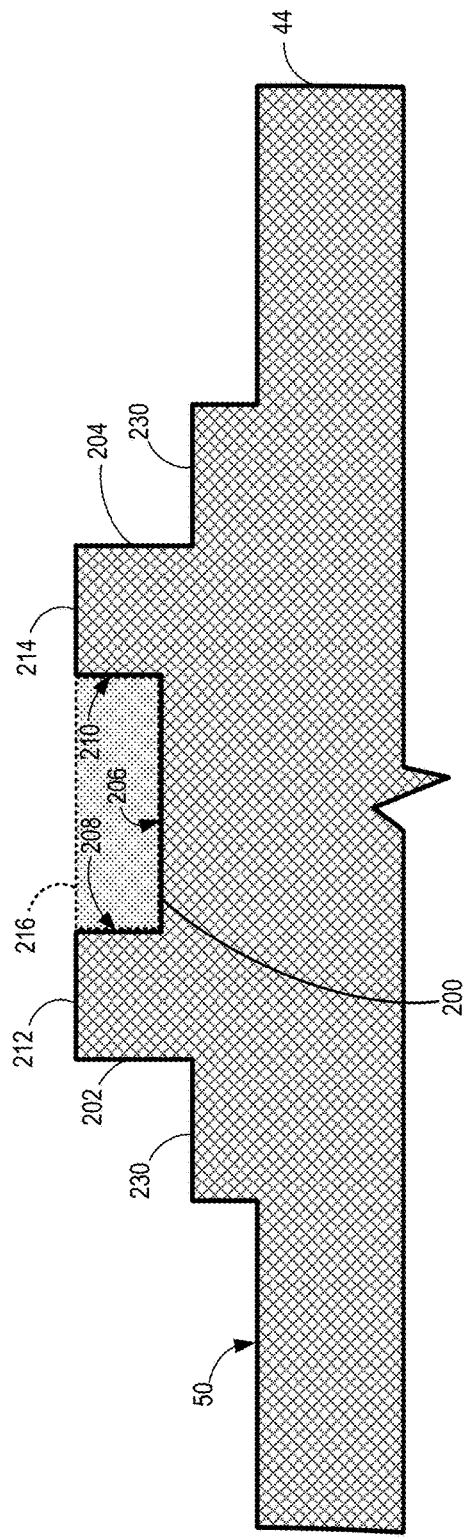

APPARATUS AND METHOD OF MANUFACTURING AN ELASTIC COMPOSITE STRUCTURE FOR AN ABSORBENT SANITARY PRODUCT

CROSS-REFERENCE TO RELATED APPLICATIONS

The present invention claims priority to U.S. Provisional Patent Application Ser. No. 62/789,058 filed Jan. 7, 2019, the disclosure of which is incorporated herein by reference in its entirety.

BACKGROUND OF THE INVENTION

Embodiments of the invention relate generally to absorbent sanitary products and, more particularly, to an improved apparatus and method for manufacturing an elastic composite structure for use in an absorbent sanitary product that minimizes or eliminates the use of consumable adhesives such as glue.

Absorbent sanitary products, such as disposable diapers, are typically equipped with elastic composite structures that include one or more elastic threads. These elastic composite structures are positioned at various locations throughout the product, including in the waistbands, leg cuff regions, and throughout all or portions of the front or back panels of the product. During the typical manufacturing process of an elastic composite structure, the elastic threads are held in a tensioned state and an adhesive is used to secure the elastic threads between the two facing layers of non-woven materials or webs. The tension in the elastic threads is subsequently released, causing the web material to pucker or fold in the areas that contain the adhered elastic threads.

The use of adhesives to bond the elastic threads within elastic composite structures presents a number of disadvantages in both the end product and manufacturing method, including costs associated with the consumable material and undesirable tactile properties of the end product (e.g., stiffness). While thermal or ultrasonic welding techniques have been proposed as alternatives for bonding elastic threads within an elastic composite structure, movement or shifting of the elastic threads between or outside of notches on the anvil during the manufacturing process may result in a given elastic thread breaking or being unanchored over one or more portions of its length.

Accordingly, there is a need for an improved apparatus and method for fabricating an elastic composite structure of an absorbent sanitary product that reduces thread breakage and improves the reliability of bonds that anchor elastic threads in position within an elastic composite structure. It would further be desirable for such an apparatus and method to eliminate or minimize the use of consumable adhesives to secure the elastic threads to the facing web layers.

BRIEF DESCRIPTION OF THE INVENTION

In accordance with one aspect of the invention, an apparatus for manufacturing an elastic composite structure includes at least one means for transporting a first web layer and a second web layer in a machine direction and at least one means for transporting an elastic thread in the machine direction in a tensioned state. The apparatus also includes a bonding unit configured to bond the first web layer to the second web layer via a bond pattern comprising at least one bond line having at least one pair of adjacent bonds and anchor the elastic thread within a passage defined by the at least one pair of adjacent bonds, the passage having a cross-sectional area smaller than a cross-sectional area of the elastic thread in a non-tensioned state.

In accordance with another aspect of the invention, a method of manufacturing an elastic composite structure includes positioning at least one tensioned elastic thread between a first web layer and a second web layer and bonding the first web layer to the second web layer via a bond pattern comprising at least one bond line having at least one pair of adjacent bonds. The method also includes anchoring the at least one elastic thread within a passage formed between the first web layer, the second web layer, and facing edges of the at least one pair of adjacent bonds, wherein the passage has a cross-sectional area that is smaller than a cross-sectional area of the at least one elastic thread in a non-tensioned state.

In accordance with another aspect of the invention, an elastic composite structure includes a first web layer, a second web layer coupled to the first web layer by a bond pattern comprising at least one bond line having at least one pair of adjacent bonds, and at least one elastic thread extending through a passage defined by facing edges of the at least one pair of adjacent bonds. The passage has a cross-sectional area that is smaller than a cross-sectional area of the at least one elastic thread in a non-tensioned state.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings:

FIG. 2 is a schematic perspective view of a portion of the manufacturing line illustrated in FIG. 1.

FIG. 9 is a cross-sectional view of a portion of a bonding unit usable with the manufacturing line of FIG. 1, according to another embodiment of the invention.

FIG. 10 is a cross-sectional view of a portion of a bonding unit usable with the manufacturing line of FIG. 1, according to another embodiment of the invention.

DETAILED DESCRIPTION

Embodiments of the present invention provide for a method and apparatus for manufacturing an elastic composite structure usable in an absorbent sanitary product such as, for example, a diaper, disposable adult pant, or feminine care product.

During the manufacture of absorbent sanitary products, it is often desirable to secure elastic threads between facing layers of non-woven material to form contoured or elasticized regions within the product. Such products are typically manufactured on an assembly or manufacturing line in which the product moves substantially continually longitudinally in what is referred to as the "machine direction."

Figure 1:
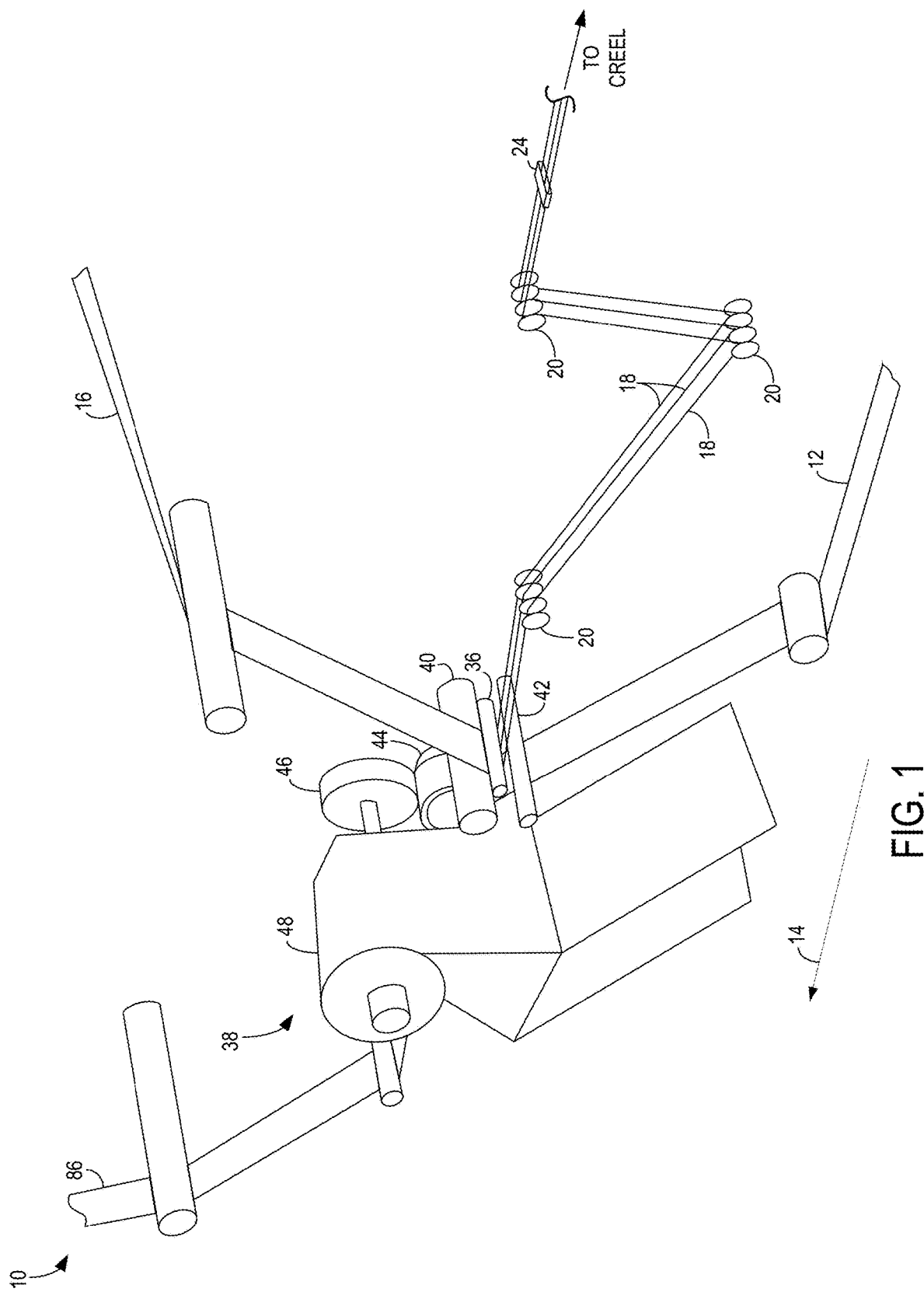
FIG. 1 is a schematic perspective view of a portion of a manufacturing line for fabricating an elastic composite structure.

Referring now to FIG. 1, a portion of an exemplary manufacturing line 10 is illustrated according to one embodiment of the invention. As shown, a first web layer 12 is fed in the machine direction 14. A second web layer 16 is similarly fed in the machine direction 14. First web layer 12 and second web layer 16 are materials capable of fusing to one another upon application of an applied energy that causes one or both of the webs 12, 16 to soften or melt and join together. First and second web layers 12, 16 may be the same type of material or different materials according to alternative embodiments. As non-limiting examples, first and second web layers 12, 16 may include nonwoven materials, woven materials, films, foams, and/or composites or laminates of any of these material types.

A series of individual elastic threads 18 are positioned between the first and second web layers 12, 16. The elastic threads 18 travel in the machine direction 14 under tension from a creel assembly (not shown) or similar device. The elastic threads 18 may be composed of any suitable elastic material including, for example, sheets, strands or ribbons of thermoplastic elastomers, natural or synthetic rubber, or LYCRA, as non-limiting examples. Each elastic thread 18 may be provided in the form of an individual elastomeric strand or be a manufactured multifilament product that includes many individual elastomeric filaments joined together, such as by a dry-spinning manufacturing process, to form a single, coalesced elastic thread 18. Each elastic thread 18 may be in the range of approximately 200-1500 decitex (dTex), in non-limiting embodiments. In an embodiment where an elastic thread 18 is a multifilament product, the elastic thread 18 may have an overall decitex of 400 dTex, in an exemplary and non-limiting embodiment, with the individual elastomeric filaments of the elastic thread 18 individually having a decitex of ten percent or less of the overall 400 dTex value. As just a few examples, a multifilament thread with a decitex of 680 and up may include 55 individual elastomeric filaments while a multifilament thread with a decitex lower than 680 may include 47 individual elastomeric filaments.

Figure 14:
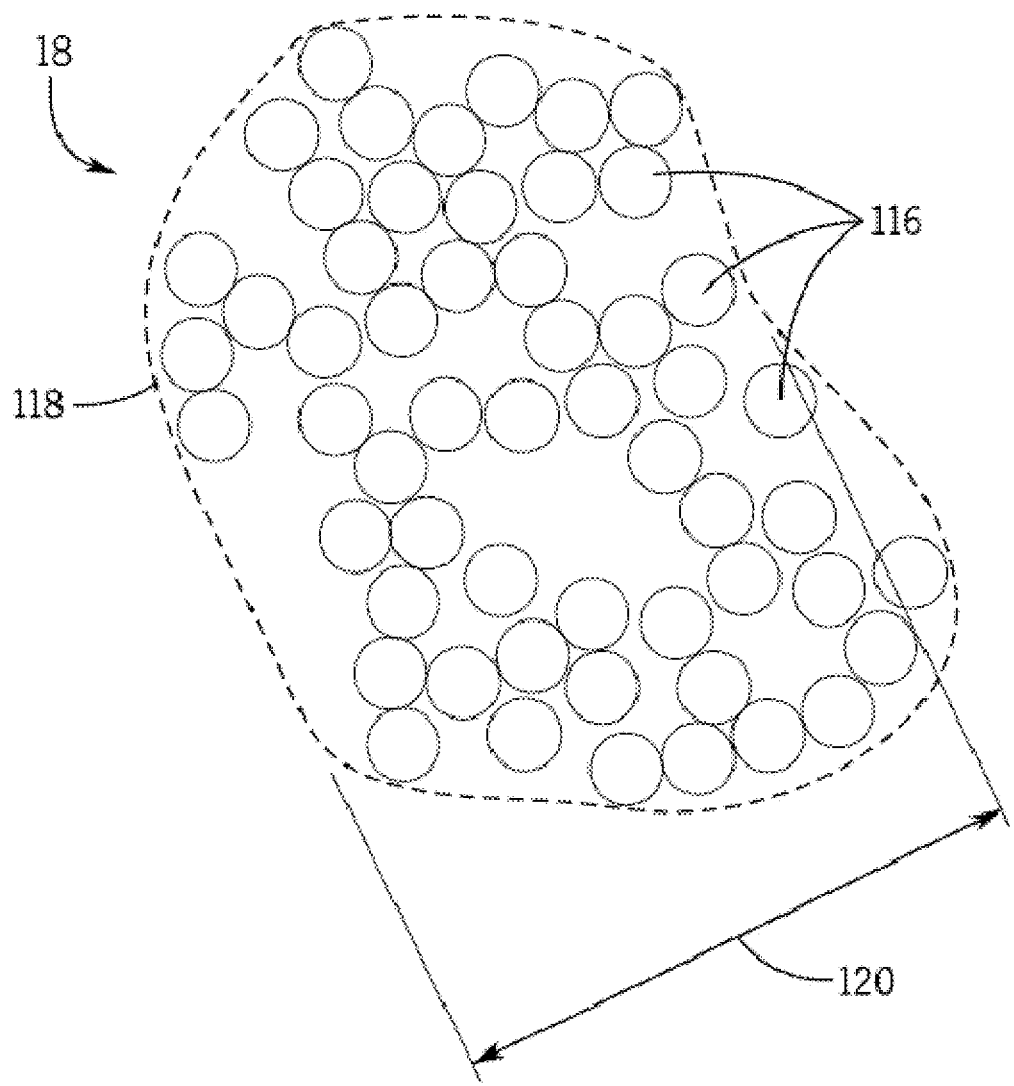
FIG. 14 is a cross-sectional view of a multifilament elastic thread usable to manufacture the elastic composite structure of FIG. 13.

Elastic threads 18 may have any suitable cross-sectional shape that facilitates formation of an elastic composite structure having desired elasticity, visual aesthetic, and manufacturability. As non-limiting examples, elastic threads 18 may have a cross-sectional shape that is round, rectangular, square, or irregular as may be the case where each elastic thread 18 is a multifilament product (as illustrated in detail in FIG. 14).

While first web layer 12 and second web layer 16 are depicted in FIG. 1 and described herein as physically separate components, it is contemplated that alternative embodiments may utilize a unitary web structure that is folded to capture the elastic threads 18 between upper and lower layers of the unitary web structure. In such an embodiment, the portion of the unitary structure positioned below the elastic threads 18 would be referred to as the first web layer 12 and the portion of the unitary structure positioned above the elastic threads 18 would be referred to as the second web layer 16.

Manufacturing line 10 includes one or more guide rollers 20 that are employed to transport, accurately position and (optionally) tension the elastic threads 18 as it travels in the machine direction 14. In some embodiments, manufacturing line 10 may include one or more optional tension monitoring devices 24 (shown in phantom) that are positioned along the path of travel of the elastic threads 18. In such an embodiment, feedback from the tension monitoring devices 24 may be utilized to control the tension (i.e., elongation) in the elastic threads 18 as they travel in the machine direction 14.

As shown in further detail in FIG. 2, each respective elastic thread 18 is positioned within a respective guiding section 26 of guide rollers 20. Doing so maintains separation between the adjacent elastic threads 18. In the illustrated embodiment, guiding section 26 includes notches that aid in alignment and guiding of the elastic threads 18. Notches may be v-shaped as shown, have curved or other alternative geometries, or be omitted entirely in alternative embodiments.

Guide rollers 20 operate to accurately position and tension individual elastic threads 18 as they travel toward a strand guide roller 36 that is positioned upstream of bonding unit 38, which is referred to hereafter as ultrasonic bonding apparatus 38. Manufacturing line 10 also includes one or more structures that are configured to transport and guide the first and second web layers 12, 16 in the machine direction 14. In the illustrated embodiment, these guide structures include an upper roller 40 and a lower roller 42 are positioned to guide the first web layer 12 and the second web layer 16, respectively, toward the ultrasonic bonding apparatus 38.

Ultrasonic bonding apparatus 38 may be a rotary ultrasonic welding system or a blade ultrasonic welding system in alternative embodiments. In the illustrated embodiment, ultrasonic bonding apparatus 38 is a rotary ultrasonic welding system that includes a rotary anvil 44 and a horn 46 that cooperate with each other to bond the first web layer 12 to the second web layer 16. The elastic threads 18 are secured or anchored in position relative to the first and second web layers 12, 16 as described in detail below. Ultrasonic bonding apparatus 38 also includes one or more frames 48 that support and/or house a motor (not shown) that drives the horn 46, a vibration control unit (not shown) that causes the horn 46 to vibrate, and a second motor (not shown) that drives the anvil 44. The horn 46 and anvil 44 are positioned in a spaced relationship relative to one another to facilitate ultrasonically bonding the first and second web layers 12, 16 to one another while the elastic threads 18 are held in tension in the space between the horn 46 and anvil 44. While horn 46 is illustrated as a rotary horn in FIG. 1, a stationary horn may be used in alternative embodiments.

The face 50 of the anvil 44 includes an arrangement of projections and notches that facilitate securing the combined elastic thread assemblies 34 in position relative to the first and second web layers 12, 16. Exemplary embodiments of this arrangement of projections and notches are described in detail below relative to FIGS. 3-11. In one non-limiting embodiment, the face 52 of the horn 46 has a smooth or substantially smooth surface contour. In alternative embodiments, face 52 may include an arrangement of projections and/or notches that mate or align with the surface pattern of the anvil 44 to further facilitate bonding the first and second web layers 12, 16 together and securing the elastic threads 18 in position relative to the first and second web layers 12, 16.

While embodiments of the invention are described relative to an ultrasonic bonding assembly and ultrasonic bonding technique, it is contemplated that the techniques described herein may be extended to any other known thermal or pressure bonding techniques.

FIG. 2 is a view of a portion of the manufacturing line 10 upstream of the ultrasonic bonding apparatus 38 looking into the machine direction 14. As shown, the elastic threads 18 are fed outward from respective guiding sections 26 in the guide rollers 20 and toward strand guide roller 36. In the embodiment, strand guide roller 36 includes an array of notches 54 that aid in aligning and guiding the elastic threads as they are received between the horn 46 and anvil 44. These notches 54 may be evenly spaced across all of the strand guide roller 36 in the manner shown or may span only a portion thereof in an alternative embodiment. In yet other embodiments, the notches 54 may be positioned at uneven intervals along the length of strand guide roller 36 depending upon design specifications and the desired placement and spacing of the elastic threads 18 in the resulting elastic composite structure.

Figure 3:
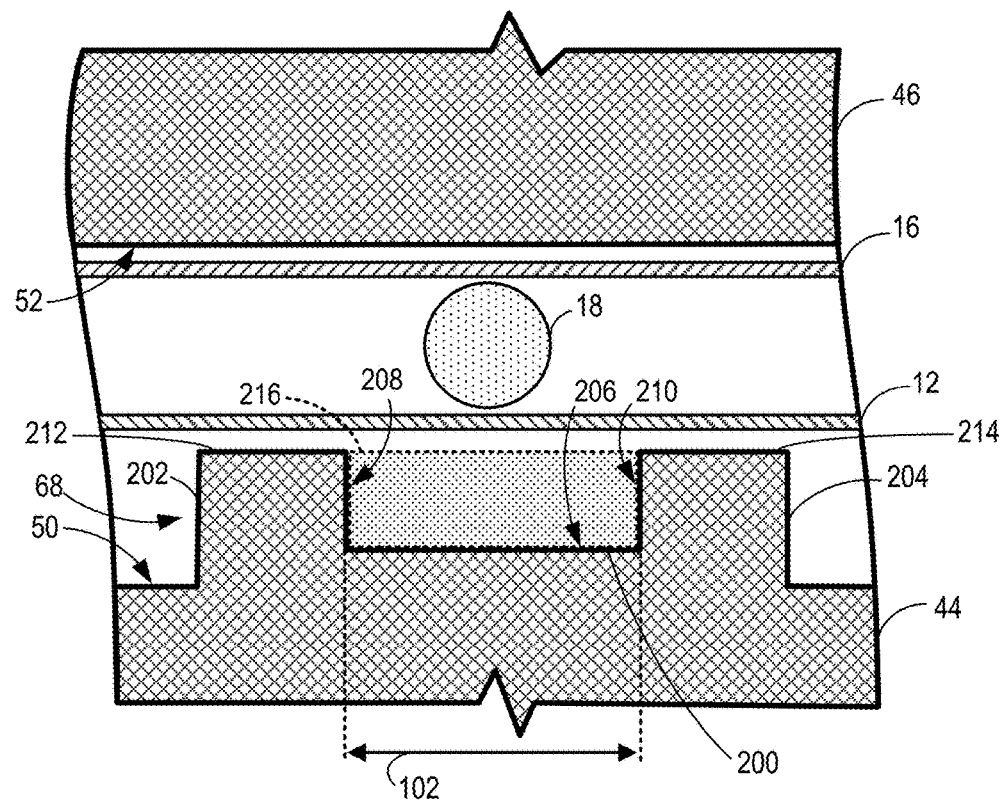
FIG. 3 is a cross-sectional view of a portion of a bonding unit usable with the manufacturing line of FIG. 1, according to one embodiment of the invention.

Referring now to FIG. 3, a cross-sectional view of a portion of the anvil 44 and horn 46 is provided according to one embodiment of the invention. As shown, the face 50 of the anvil 44 includes a welding line 68 that is defined by at least one notch 200, which is positioned between a corresponding pair of projections 202, 204. While only one instance of a notch 200 and corresponding pair of projections 202, 204 is illustrated in FIG. 3, it is contemplated that each welding line 68 on the anvil 44 may alternatively include multiple notches 200, with each notch 200 similarly arranged between a corresponding pair of projections 202, 204. In the embodiment shown, notch 200 has a u-shaped geometry defined by a bottom surface 206 and facing surfaces 208, 210 of the projections 202, 204. One or more of surfaces 206, 208, 210 may be planar, as shown, or curved in alternative embodiments.

Figure 4A:
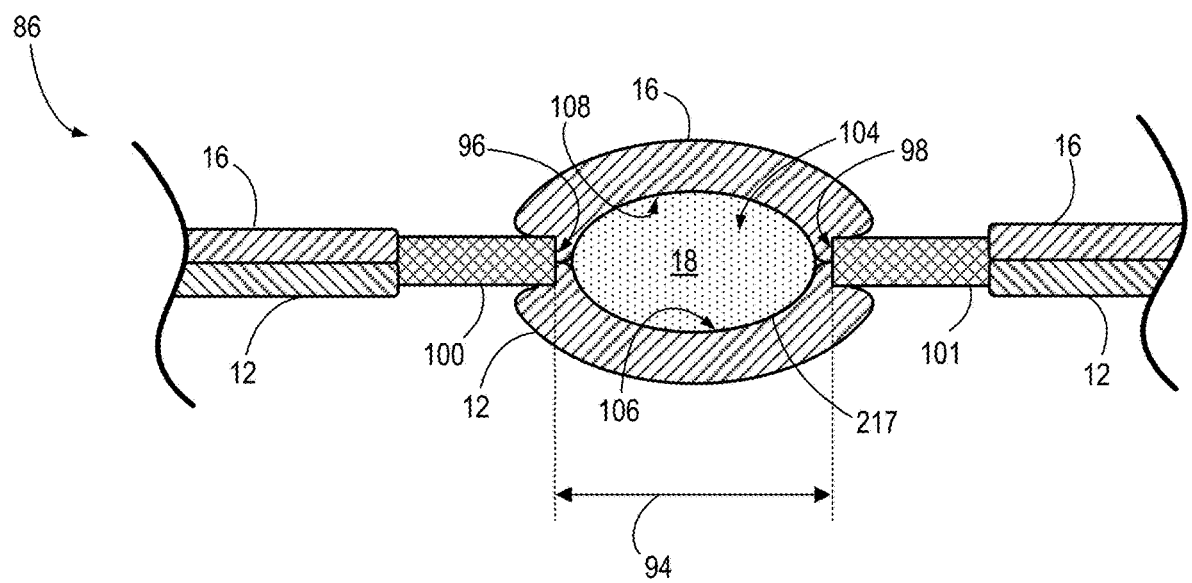
FIG. 4A is a cross-sectional view of a portion of an elastic composite structure fabricated using the bonding unit of FIG. 3 in its relaxed or non-tensioned state, according to one embodiment of the invention.
Figure 4B:
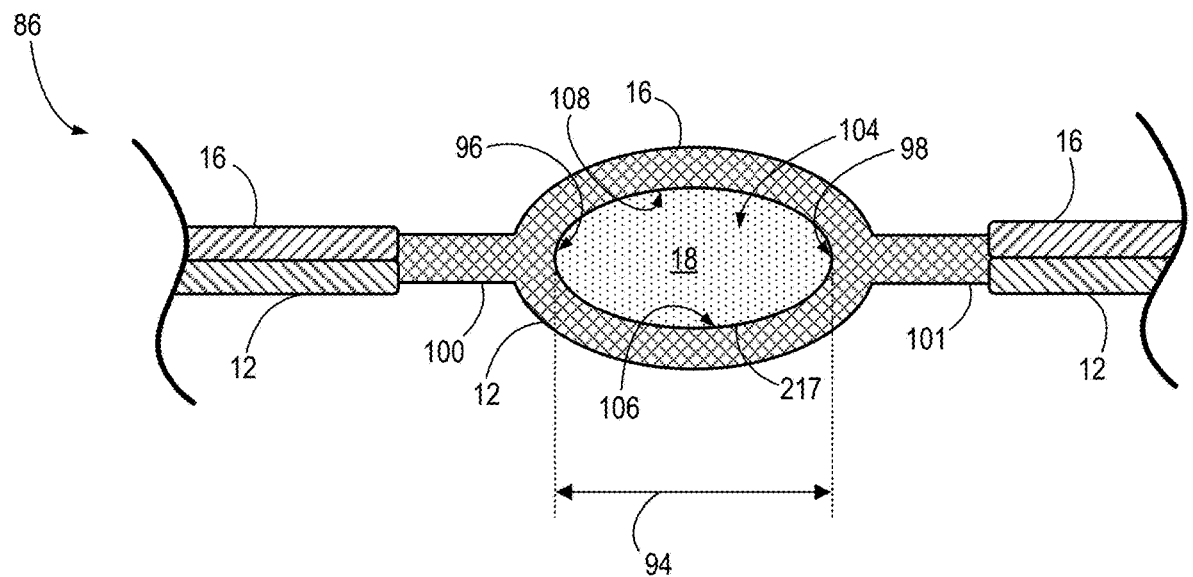
FIG. 4B is a cross-sectional view of a portion of an elastic composite structure fabricated using the bonding unit of FIG. 3 in its relaxed or non-tensioned state, according to another embodiment of the invention.

During the manufacturing process, the first and second web layers 12, 16 are positioned between the face 50 of the anvil 44 and the face 52 of the horn 46. An elastic thread 18 is positioned between the first and second web layers 12, 16 in a tensioned state and aligned above notch 200. As shown in FIGS. 4A and 4B and with continued reference to FIG. 3, the first and second web layers 12, 16 are bonded together by a pair of bonds 100, 101 at locations corresponding to the land surfaces 212, 214 of the respective projections 202, 204. Thus bonds 100, 101 each have a width that corresponds to the width of land surfaces 212, 214. Depending on the operating parameters of the ultrasonic bonding apparatus 38 and/or the geometry and configuration of the notches and projections on the anvil and/or horn, the resulting pair of adjacent bonds 100, 101 either may be discrete, discontinuous bonds 100, 101 as shown in FIG. 4A, or part of a continuous fusion bond 103 that fuses the facing web layers 12, 15 together at bond points 100, 101 and fuses one or both of the facing web layers 12, 16 to the elastic thread 18, as shown in FIG. 4B. The bonding operation creates a manufactured elastic composite structure 86 as shown in FIG. 13.

Figure 5:
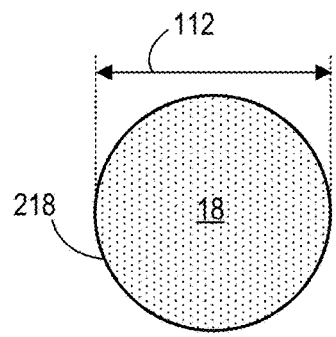
FIG. 5 is a cross-sectional view of an exemplary elastic strand of the elastic composite structure of FIG. 4 in its relaxed or non-tensioned state.
Figure 13A:
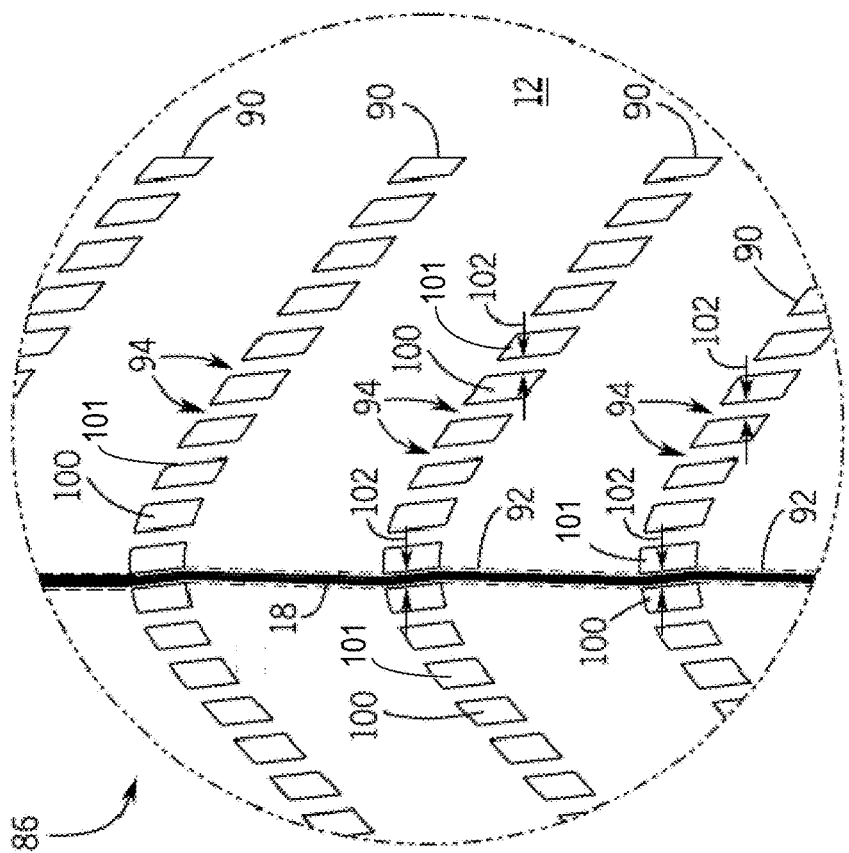
FIG. 13A is a detailed view of a portion of the elastic composite structure of FIG. 13 shown in its elongated or tensioned state.
Figure 13:
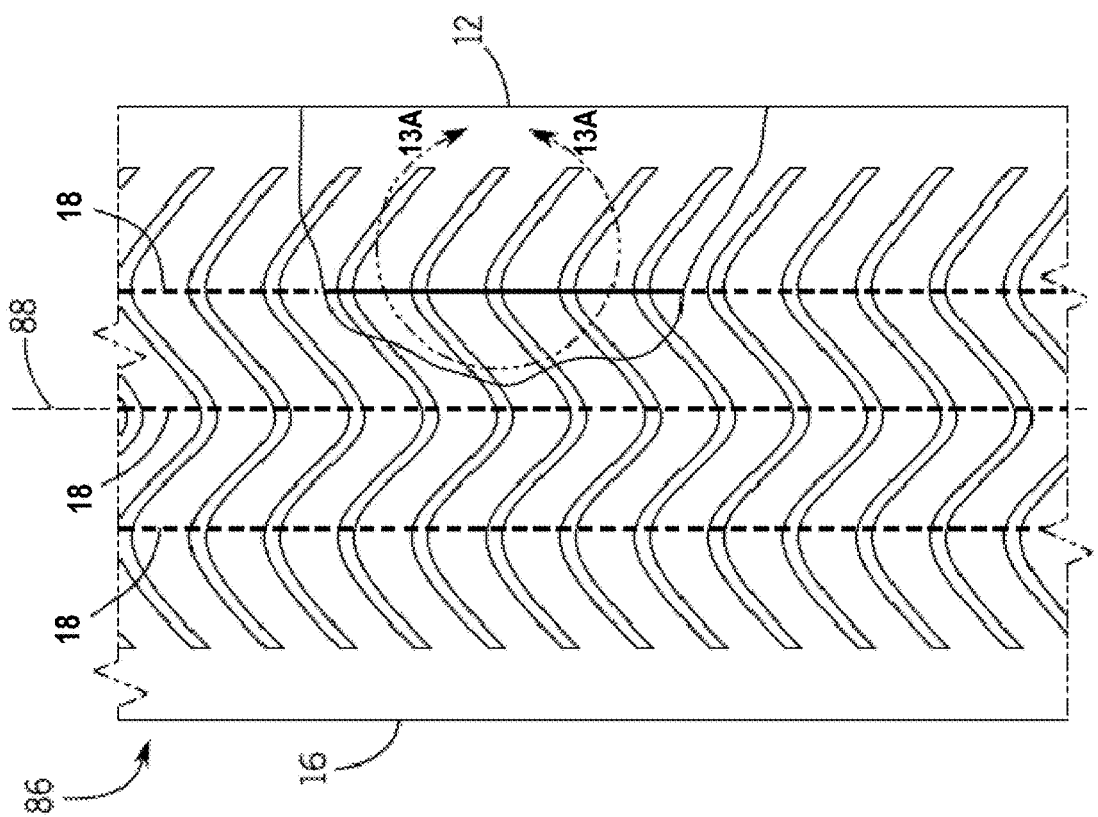
FIG. 13 is a top view of a portion of an elastic composite structure shown in its elongated or tensioned state, according to an embodiment of the invention.

When the manufactured elastic composite structure 86 shown in FIG. 13 is permitted to relax, each elastic thread 18 will attempt to swell or expand to return to its non-tensioned or relaxed state within passage 104. Passage 104 has a cross-sectional area 217 that is dictated by the cross-sectional area 216 of the notch 200 on anvil 44. Thus, the cross-sectional area 217 of passage 104 is equal to or substantially equal to the cross-sectional area 216 of the notch 200. Notch 200 is sized to have a cross-sectional area 216 that is less than the cross-sectional area 218 of the elastic thread 18 in its non-tensioned or relaxed state, which is illustrated in FIG. 5. As the elastic thread 18 expands, it becomes anchored or trapped in the passage 104 formed between the upward facing surface 106 of the first web layer 12, the downward facing surface 108 of the second web layer 16, and the facing edges 96, 98 of a pair of adjacent bonds 100, 101.

As shown in FIG. 4, the elastic thread 18 deforms as it expands due to the relatively shallow geometry of the notch 200. Depending on the shape and dimensions of notch 200 and the cross-sectional area 218 of the non-tensioned elastic thread 18, the elastic thread 18 may expand to completely fill the passage 104, as shown in FIG. 4. Alternatively, the elastic thread 18 may expand to a position where the elastic thread 18 fills only a portion of the passage 104. In such an embodiment, the portion of the elastic thread 18 adjacent bonds 100, 101 would be secured in position relative to web layers 12, 16 by virtue of contact between the elastic thread 18 and facing surfaces 106, 108 of the web layers 12, 16 with a gap formed between the elastic thread 18 and one or both of the facing edges 96, 98 of adjacent bonds 100, 101.

Figure 6:
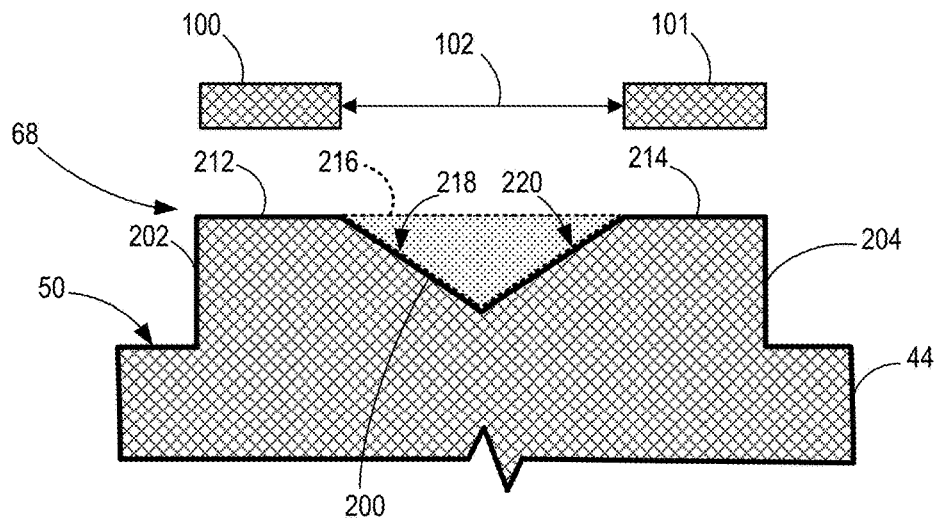
FIG. 6 is a cross-sectional view of a portion of a bonding unit usable with the manufacturing line of FIG. 1, according to another embodiment of the invention.
Figure 7:
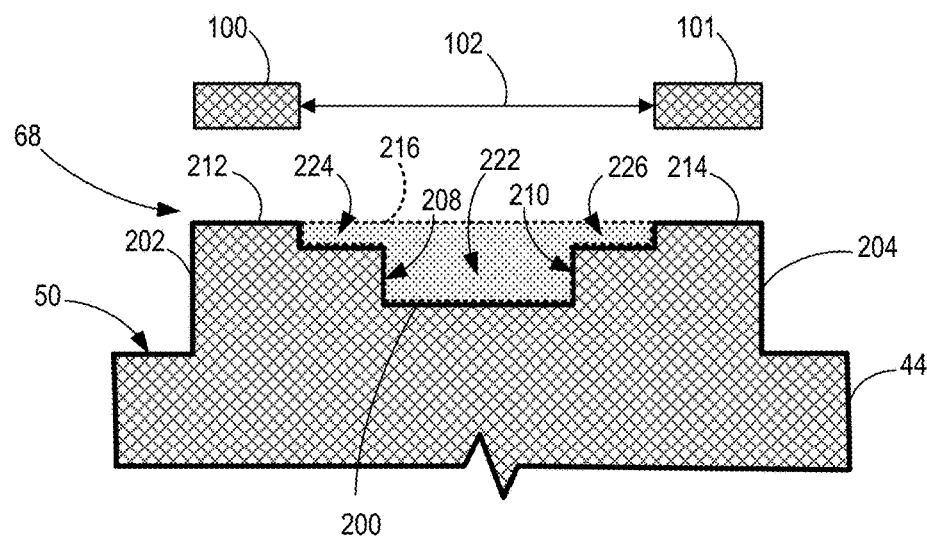
FIG. 7 is a cross-sectional view of a portion of a bonding unit usable with the manufacturing line of FIG. 1, according to another embodiment of the invention.
Figure 8:
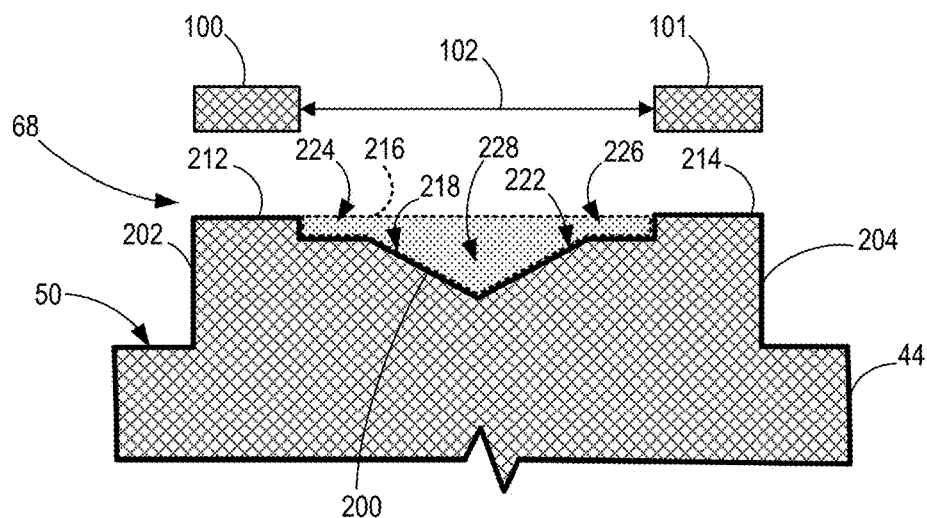
FIG. 8 is a cross-sectional view of a portion of a bonding unit usable with the manufacturing line of FIG. 1, according to another embodiment of the invention.

FIGS. 6, 7, 8, and 9 depict notch configurations according to alternative embodiments of the invention. A cross-sectional view of the resulting pair of adjacent bonds 100, 101 between the first and second web layers 12, 16 is provided above the land surfaces 212, 214 of the respective projections 202, 204 for ease of reference. Other portions of the elastic composite structure 86 are omitted for clarity purposes. In FIG. 6, notch 200 has a v-shaped geometry formed by opposing angled surfaces 218, 220. The notches 200 in FIGS. 7 and 8 have stepped configurations. In FIG. 7, notch 200 includes a u-shaped central region 222 defined by bottom surface 206 and two facing surfaces 208, 210 and two opposing side regions 224, 226. The notch 200 of FIG. 8 includes similarly configured side regions 224, 226 with a v-shaped central region 228 defined by opposing angled surfaces 218, 220. FIG. 9 depicts a modified stepped geometry where the angled surfaces 218, 220 of notch 200 have a different slope in the central region 228 of the notch 200 than in the opposing side regions 224, 226. The surfaces that define the notches 200 in FIGS. 6-9 may be straight, as shown, curved, or some mixture of curved and straight in alternative embodiments.

Each of notches 200 in FIGS. 6-9 has a cross sectional area 216 that is smaller than the cross-sectional area of the elastic thread 18 in its non-tensioned state. The notches 200 of FIGS. 6-9 define a resulting pair of adjacent bonds 100, 101 that are spaced apart by a gap or distance 102 that is greater than the strand diameter 112 of the elastic thread 18 when in its non-tensioned state.

As used herein the phrase "strand diameter" refers to the smallest measurable cross-sectional width of the elastic thread 18 in its non-tensioned state. In embodiments where a given elastic thread 18 is a monofilament structure, the strand diameter is the minor diameter or smallest measurable width of the monofilament structure in its non-tensioned state. In embodiments where a given elastic thread 18 is a structure that includes many individual filaments 116 (i.e., elastic thread 18 is a multi-filament structure), the elastic thread 18 typically will have an irregular cross-sectional area similar to that shown in FIG. 14. The strand diameter of such a multifilament structure is to be understood as the smallest distance 120 between opposite edges of an outline that generally defines the irregular cross-sectional area. The cross-sectional area of the multifilament structure may be measured as the cross-sectional area within a perimeter 118 drawn to surround all of the individual filaments 116 or calculated as the summed total of the cross-sectional area of each of the individual filaments 116.

FIG. 10 depicts a portion of anvil 44 according to yet another embodiment of the invention. In this embodiment, notch 200 and the pair of flanking projections 202, 204 are formed atop a step 230 that is elevated above the face 50 of the anvil 44. While only one notch 200 and corresponding pair of projections 202, 204 is illustrated atop step 230, alternative embodiments may include any number of notches 200 and corresponding projections 202, 204. Notch 200 may have the u-shaped geometry shown in FIG. 3 or any of the alternative notch geometries illustrated in FIGS. 6-9 or otherwise described herein.

Each of FIG. 3, FIG. 6, FIG. 7, FIG. 8, FIG. 9, and FIG. 10 is to be understood as illustrating one exemplary and non-limiting configuration of notch 200. In alternative embodiments, anvil 44 may include one or more notches 200 that has any shape or surface topology, including straight surfaces, curved surfaces, or any combination thereof that results in a notch 200 having a cross-sectional area 216 that is smaller than the cross-sectional area 218 of the corresponding elastic thread 18 when in its non-tensioned state.

Figure 11A:
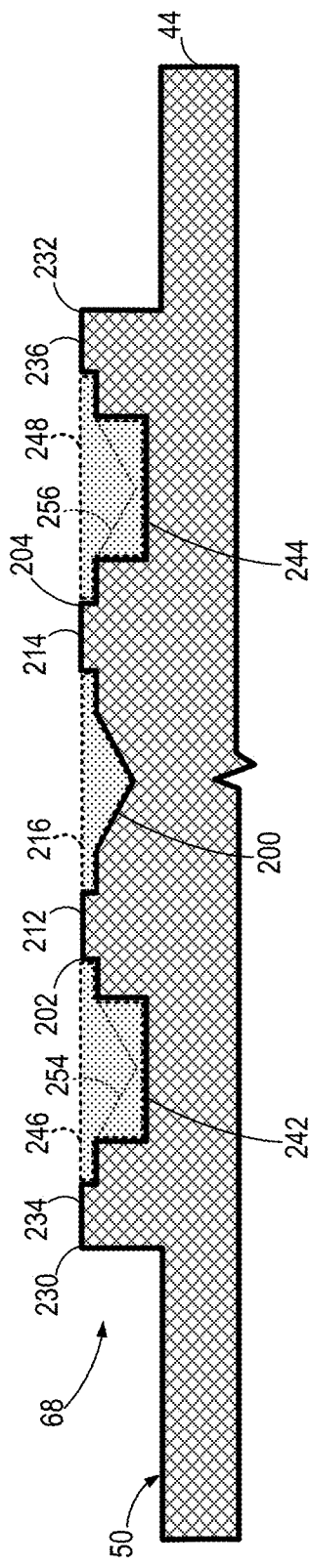
FIG. 11A is a cross-sectional view of a portion of a bonding unit usable with the manufacturing line of FIG. 1, according to another embodiment of the invention.
Figure 11B:
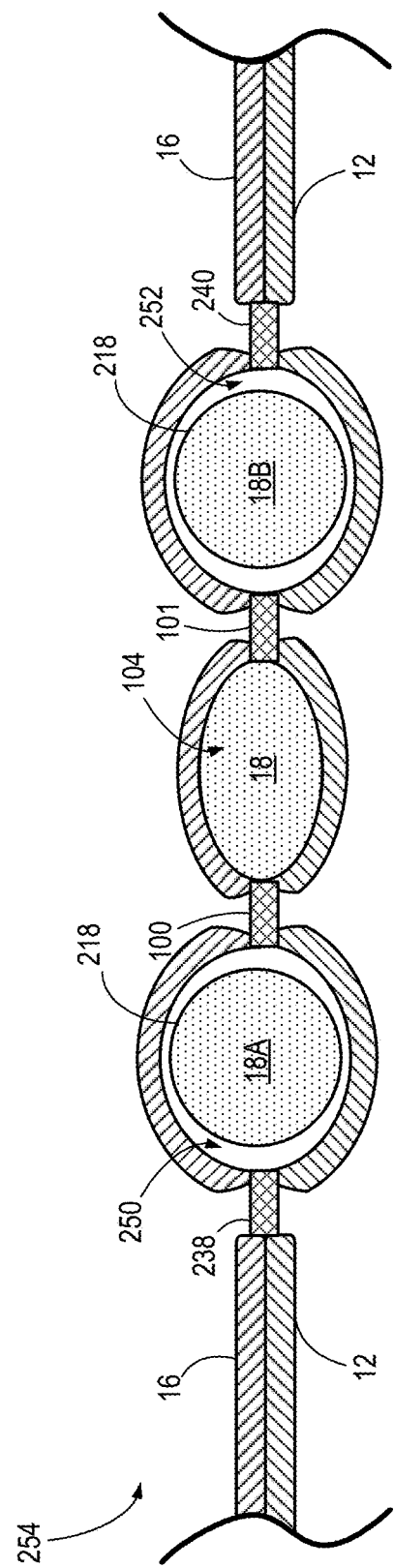
FIG. 11B is a cross-sectional view of a portion of an elastic composite structure fabricated using the bonding unit of FIG. 11A in its relaxed or non-tensioned state.

FIG. 11A depicts a portion of anvil 44 according to another embodiment of the invention. Welding line 68 of anvil 44 includes at least one notch 200 that has a cross-sectional area 216 that is smaller than the cross-sectional area 218 of a corresponding elastic thread 18 when in its non-tensioned state. Notch 200 forms a pair of adjacent bonds 100, 101 between first and second web layers 12, 16 that anchor the elastic thread 18 within a passage 104 defined between web layers 12, 16 and the pair of adjacent bonds 100, 101 as shown in FIG. 11B. Depending on the geometry of notch 200, operational parameters of ultrasonic bonding apparatus 38, and material selection of web layers 12, 16 and elastic thread 18, the resulting pair of bonds 100, 101 may be discrete, separated bond sites, similar to those shown in FIG. 4A, or connected by virtue of fusion bonding between one or both of the web layers 12, 16 and the surface of the elastic thread 18, similar to that shown and described relative to FIG. 4B. While notch 200 is depicted with a notch geometry similar to that of FIG. 8, it is contemplated that notch 200 may have any of the alternative geometries described above with respect to FIGS. 3, 6, 7, 9, and 10.

In addition to the projections 202, 204 that form bonds 100, 101, welding line 68 of FIG. 11A includes projections 230, 232 with land surfaces 234, 236 that form corresponding bonds 238, 240 between first and second web layers 12, 16. Notch 242 is defined between projection 202 and projection 230; notch 244 is defined between projection 204 and 232. Unlike notch 200, notches 242, 244 have respective cross-sectional areas 246, 248 that are larger than the cross-sectional area 218 of the corresponding elastic thread 18A, 18B when in its non-tensioned state. As shown in FIG. 11B, notches 242, 244 define passages 250, 252 between first and second web layers 12, 16 and respective bond pairs 100/238 and 101/240 in resulting elastic composite structure 254 that are larger than the cross-sectional area 218 of the non-tensioned elastic threads 18A, 18B. Elastic threads 18A, 18B are free to expand to their non-tensioned state within passages 250, 252. Bond pairs 100/238 and 101/240 thus serve to define a channel that contains elastic threads 18A and 18B but does not anchor the elastic threads 18A, 18B in position relative to first and second web layers 12, 16.

In one non-limiting embodiment notches 200, 242, and 244 of anvil 44 are manufactured using a multi-step machining process that includes machining a pattern of similarly sized "anchoring" notches on the face 50 of the anvil at the desired location of each notch 200, 242, 244. In the illustrated example, the manufacturing process would include initially machining notches 200, 242, and 244 to all have the notch geometry or profile of notch 200, as indicated by dashed lines 254, 256. In a subsequent machining step, additional material is removed from select notch locations to define the final notch geometry of the larger, non-anchoring notches 242, 244.

FIGS. 11A and 11B are to be understood as depicting one exemplary and non-limiting configuration of anchoring notch 200 and non-anchoring notches 242, 244. It is to be understood that alternative embodiments may include any combination or pattern of anchoring and non-anchoring notches 200, 242, 244 based on design considerations of the end product. Thus, a given welding line 68 may include a repeating pattern of one or more alternating anchoring notches and one or more non-anchoring notches or only one type of notch. Specific regions containing only anchoring notches or only non-anchoring notches may also be defined between two or more sequential welding lines 68 on the face 50 of the anvil 44.

Figure 12A:
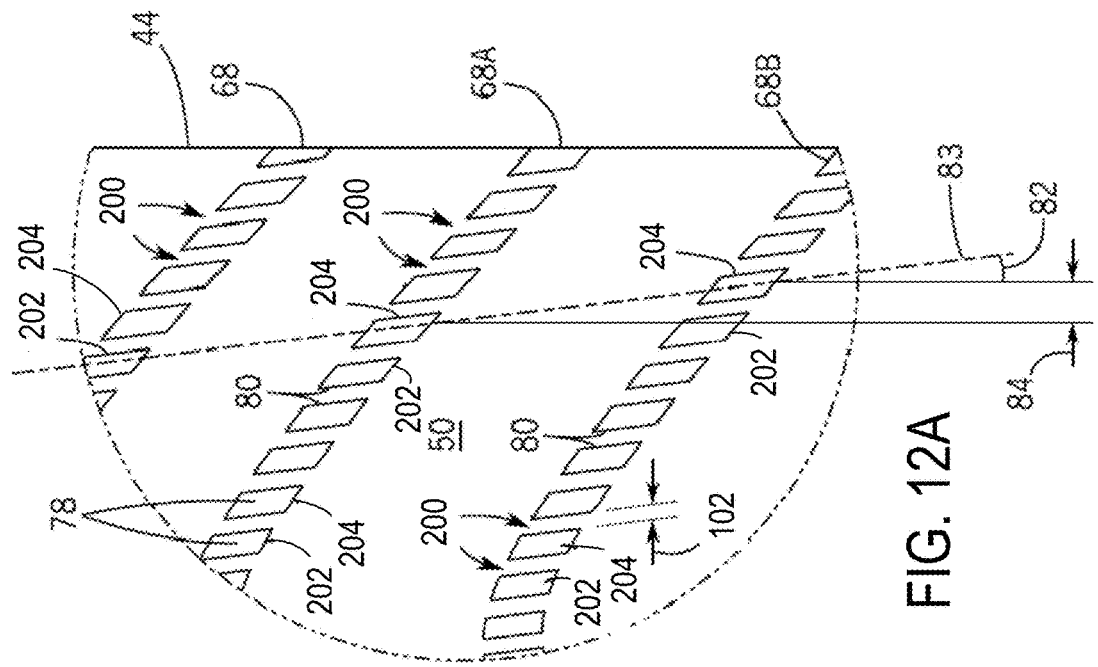
FIG. 12A is a detailed view of a portion of the rotary anvil of FIG. 12.
Figure 12:
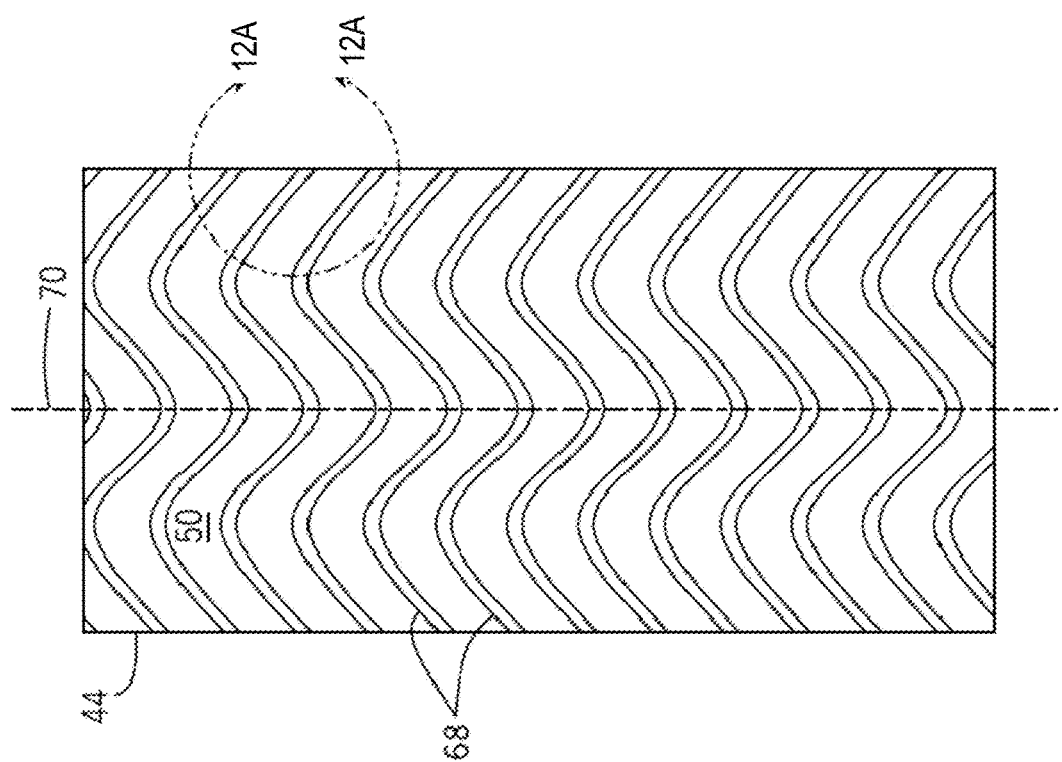
FIG. 12 is a front view of a rotary anvil usable with the manufacturing line of FIG. 1, according to an embodiment of the invention.

Referring now to FIG. 12, further details of the surface pattern of the anvil 44 is provided in accordance with one non-limiting embodiment of the invention. As shown, anvil 44 includes an array of welding lines 68 that are spaced apart from one another along the circumferential axis 70 of the anvil face 50. As shown more specifically in the detailed view provided in FIG. 12A, each welding line 68 contains a pattern of discrete projections 202, 204 that extend outward from the face 50 of the anvil 44. The projections 202, 204 are spaced apart from one another, by a gap that is defined by the width 102 of the notch 200 positioned between a given pair of adjacent projections 202, 204. Welding lines 68 are sinusoidal in the embodiment shown. However, may be straight lines, curved lines, or otherwise arranged to create a continuous and repeating pattern on the end product.

In the illustrated embodiment, the contact surfaces 78 of the projections 202, 204 have side surfaces 80 oriented at an angle 82 relative to the circumferential axis 70 such that no hypothetical arc 83 drawn from adjacent welding lines 68 is parallel to the circumferential axis 70 of the anvil 44. In such an embodiment, the facing surfaces 80 of adjacent projections 202, 204 are non-parallel to the circumferential axis 70 as shown. As a result, projections 202, 204 of adjacent welding lines 68 are not aligned with one another along the circumferential axis 70. Instead, a given projection 72A in one welding line 68A is offset from a given projection 72B in an adjacent welding line 68B by a pitch 84 defined by an angle 82. Projections 202, 204 thus define a threaded pattern that extends around the circumferential face 50 of the anvil 44.

It is contemplated that the contact surfaces 78 of the projections 202, 204 may have different geometries in alternative embodiments. As non-limiting examples, projections 202, 204 may be circular, rectangular, crescent shaped, or have irregular shapes that may be selected to form a desired overall pattern on the end product. In yet another embodiment, corresponding projections 202, 204 of adjacent welding lines 68A, 68B may be aligned with one another in a line parallel to the circumferential axis 70. Alternatively, projections 202, 204 of sequential welding lines 68A, 68B may be offset from one another in the cross-machine direction thereby defining a stepped or non-linear passage through the bond lines that are formed on the first and second web layers 12, 16.

FIG. 13 illustrates a portion of an elastic composite structure 86 output from the ultrasonic bonding apparatus 38. The elastic composite structure 86 is illustrated in an elongated state with elastic threads 18 stretched to a point where the first web layer 12 and second web layer 16 are substantially flat. As shown, the elastic composite structure 86 includes the first web layer 12, the second web layer 16, and a number of elastic threads 18 that are located between the first and second web layers 12, 16 and oriented along a longitudinal axis 88 of the elastic composite structure 86. While the illustrated embodiment includes three (3) elastic threads 18 it is contemplated that alternative embodiments may include a single elastic thread 18 or any number of multiple elastic threads 18 based on design specifications of the end product.

The ultrasonic bonding operation results in a continuous and repeating pattern of bond lines 90 that mirror the welding lines 68 on the anvil 44 and bond or fuse the first web layer 12 to the second web layer 16. Thus, in embodiments where welding lines 68 are sinusoidal, the resulting bond lines 90 have a similar sinusoidal bond pattern. As shown in the detailed view provided in FIG. 13A, the tensioned elastic threads 18 extend along a passage 92 that is bounded by the gap 94 formed between the facing edges 96, 98 of a pair of adjacent bonds 100, 101 in each subsequent bond line 90. The gap 94 has a width defined by the width 102 of the notches 200 on the anvil 44. In the regions between the bond lines 90, the elastic threads 18 are free to swell or expand to their non-tensioned state. In their non-tensioned state, each elastic thread 18 has a cross-sectional area 218 that is smaller than the cross-sectional area of the passage 104 formed between each pair of adjacent bonds 100, 101 and the first and second web layers 12, 16. As a result, the elastic thread 18 is trapped or anchored between adjacent pairs of bonds 100, 101 and the first and second web layers 12, 16.

The apparatus and methods described herein can be used to make elastic composite structures for waist regions, below-waist regions, and/or leg cuff regions of a single-piece or three-piece diaper, as non-limiting examples, without the use of glue. By eliminating the use of glue, the resulting elastic composite is softer to the touch and has a more uniform ruffling pattern in the cross-machine direction (i.e., the direction perpendicular to the machine direction). From a manufacturing standpoint, the elastic threads are anchored within dedicated passages of the elastic composite structure that are defined based on notch geometries of the bonding assembly that improve the reliability of the bonds that anchor the elastic threads in position and reducing the likelihood of thread breakage during manufacture. Accordingly, embodiments of the invention disclosed herein provide a more reliable manufacturing process than existing prior art approaches and result in an end product that is visually and tactilely more pleasing to the end customer.

Therefore, according to one embodiment of the invention, an apparatus for manufacturing an elastic composite structure includes at least one means for transporting a first web layer and a second web layer in a machine direction and at least one means for transporting an elastic thread in the machine direction in a tensioned state. The apparatus also includes a bonding unit configured to bond the first web layer to the second web layer via a bond pattern comprising at least one bond line having at least one pair of adjacent bonds and anchor the elastic thread within a passage defined by the at least one pair of adjacent bonds, the passage having a cross-sectional area smaller than a cross-sectional area of the elastic thread in a non-tensioned state.

According to another embodiment of the invention, a method of manufacturing an elastic composite structure includes positioning at least one tensioned elastic thread between a first web layer and a second web layer and bonding the first web layer to the second web layer via a bond pattern comprising at least one bond line having at least one pair of adjacent bonds. The method also includes anchoring the at least one elastic thread within a passage formed between the first web layer, the second web layer, and facing edges of the at least one pair of adjacent bonds, wherein the passage has a cross-sectional area that is smaller than a cross-sectional area of the at least one elastic thread in a non-tensioned state.

According to yet another embodiment of the invention, an elastic composite structure includes a first web layer, a second web layer coupled to the first web layer by a bond pattern comprising at least one bond line having at least one pair of adjacent bonds, and at least one elastic thread extending through a passage defined by facing edges of the at least one pair of adjacent bonds. The passage has a cross-sectional area that is smaller than a cross-sectional area of the at least one elastic thread in a non-tensioned state.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:
1. An apparatus for manufacturing an elastic composite structure, the apparatus comprising:
   at least one means for transporting a first web layer and a second web layer in a machine direction;

at least one means for transporting an elastic thread in the machine direction in a tensioned state; and a bonding unit configured to:

bond the first web layer to the second web layer absent adhesive via a bond pattern comprising at least one bond line having at least one pair of adjacent bonds; and anchor the elastic thread within a passage defined by the at least one pair of adjacent bonds, the passage having a cross-sectional area smaller than a cross-sectional area of the elastic thread in a non-tensioned state;

wherein the bonding unit comprises an ultrasonic bonding unit having a face with at least one welding line defined thereon, each welding line of the at least one welding line arranged to form the bond pattern;

wherein the at least one welding line comprises a notch positioned between a pair of projections;

wherein the notch has a cross-sectional area that is smaller than the cross-sectional area of the elastic thread in the non-tensioned state, and wherein the notch has a stepped geometry.

2. The apparatus of claim 1 wherein facing surfaces of the at least one pair of adjacent bonds are spaced apart at a distance greater than a strand diameter of the elastic thread in the non-tensioned state.

3. The apparatus of claim 1 wherein the notch is v-shaped.

4. The apparatus of claim 1 wherein facing edges of the at least one pair of adjacent bonds are spaced at a distance greater than a diameter of the at least one elastic thread in the non-tensioned state.

5. The apparatus of claim 1 further comprising an ultrasonic bond between the first web layer and the second web layer.

6. The apparatus of claim 1 wherein the at least one notch has one of a v-shaped geometry and a u-shaped geometry.

* * * * *